(12) United States Patent
Bretschneider et al.

(10) Patent No.: US 8,536,204 B2
(45) Date of Patent: Sep. 17, 2013

(54) AMIDES AND THIOAMIDES AS PESTICIDES

(75) Inventors: Thomas Bretschneider, Lohmar (DE); Arnd Voerste, Köln (DE); Martin Füßlein, Düsseldorf (DE); Adeline Köhler, Wuppertal (DE); Ulrich Görgens, Ratingen (DE)

(73) Assignee: Bayer CropScience AG, Monheim (DE)

( * ) Notice: Subject to any disclaimer, the term of this patent is extended or adjusted under 35 U.S.C. 154(b) by 185 days.

(21) Appl. No.: 12/902,894

(22) Filed: Oct. 12, 2010

(65) Prior Publication Data

US 2011/0118290 A1     May 19, 2011

Related U.S. Application Data

(60) Provisional application No. 61/251,042, filed on Oct. 13, 2009.

(30) Foreign Application Priority Data

Oct. 12, 2009    (EP) ..................................... 09172736

(51) Int. Cl.
*A01N 43/40*        (2006.01)
*C07D 401/04*     (2006.01)

(52) U.S. Cl.
USPC ...................... 514/341; 546/275.4; 546/276.1

(58) Field of Classification Search
USPC ............................. 546/275.4, 276.1; 514/341
See application file for complete search history.

(56) References Cited

U.S. PATENT DOCUMENTS

| | | | |
|---|---|---|---|
| 4,080,457 | A | 3/1978 | Harrison et al. |
| 2006/0281780 | A1 | 12/2006 | Goto et al. |
| 2007/0129407 | A1 | 6/2007 | Koyanagi et al. |
| 2008/0305955 | A1 | 12/2008 | Bretschneider et al. |
| 2009/0036310 | A1 | 2/2009 | Jakobi et al. |
| 2009/0076282 | A1 | 3/2009 | Toriyabe et al. |
| 2009/0247551 | A1 | 10/2009 | Jeschke et al. |
| 2009/0253749 | A1 | 10/2009 | Jeschke et al. |
| 2010/0029478 | A1 | 2/2010 | Alig et al. |
| 2010/0240705 | A1 | 9/2010 | Jeschke et al. |
| 2011/0021539 | A1 | 1/2011 | Schwarz et al. |
| 2011/0124660 | A1 | 5/2011 | Schwarz et al. |
| 2011/0166143 | A1 | 7/2011 | Bretschneider et al. |
| 2011/0190365 | A1 | 8/2011 | Werner et al. |
| 2012/0165345 | A1 | 6/2012 | Bretschneider et al. |

FOREIGN PATENT DOCUMENTS

| | | |
|---|---|---|
| CA | 2 671 179 A1 | 6/2008 |
| DE | 2 221 647 | 11/1972 |
| DE | 10 2006 032 168 A1 | 12/2007 |
| EP | 0 539 588 A1 | 5/1993 |
| EP | 1 938 686 A1 | 7/2008 |
| WO | WO 2005/035486 A1 | 4/2005 |
| WO | WO 2006/056433 A2 | 6/2006 |
| WO | WO 2006/100288 A2 | 9/2006 |
| WO | WO 2007/043677 A1 | 4/2007 |
| WO | WO 2007/057407 A2 | 5/2007 |
| WO | WO 2007/095229 A2 | 8/2007 |
| WO | WO 2007/149134 A1 | 12/2007 |
| WO | WO 2008/104503 A1 | 9/2008 |
| WO | 2009068617 * | 6/2009 |

OTHER PUBLICATIONS

Antilla, J.C., et al., "Copper-Diamine-Catalyzed N-Arylation of Pyrroles, Pyrazoles, Indazoles, Imidazoles, and Triazoles," *J. Org. Chem.* 69(17):5578-5587, American Chemical Society, United States (2004).

Pedersen, B.S., et al., "Studies On Organophosphorus Compounds XX. Syntheses of Thioketones," *Bull. Soc. Chim. Belg.* 87(3):223-228, Sociétés Chimiques Belges, Belgium (1978).

* cited by examiner

*Primary Examiner* — Patricia L Morris
(74) *Attorney, Agent, or Firm* — Sterne, Kessler, Goldstein & Fox P.L.L.C.

(57) ABSTRACT

The present application relates to novel amides and thioamides, to processes for preparation thereof and to use thereof for controlling animal pests, in particular arthropods and especially insects.

5 Claims, No Drawings

AMIDES AND THIOAMIDES AS PESTICIDES

The present application relates to novel amides and thioamides, to processes for preparation thereof and to use thereof for controlling animal pests, which include arthropods and especially insects.

Particular amides have already become known as insecticidally active ingredients (cf. DE 2221647).

Modern crop protection compositions have to satisfy many demands, for example in relation to efficacy, persistence and spectrum of their action, and possible use. Important questions relate to toxicity, combinability with other active ingredients or formulating assistants, and another is that of the effort and expense of synthesizing an active ingredient. Moreover, resistances can occur. For all these reasons, the search for novel crop protection compositions cannot be considered to be complete, and there is a constant need for novel compounds with improved properties over the known compounds, at least in relation to individual aspects.

It was an object of the present invention to provide compounds by which the spectrum of crop protection compositions is broadened in various respects.

The object, and also further objects which are not stated explicitly and are derivable or discernible from the connections discussed herein, are achieved by novel compounds of the formula (I)

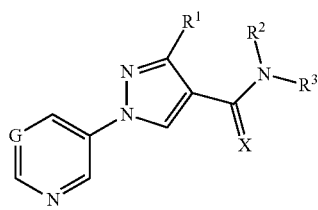

in which

G is N, CH, C-halogen, C-nitro, C-cyano, C-alkyl, C-haloalkyl, C-cycloalkyl, C-alkoxy, C-haloalkoxy, $R^1$ is hydrogen, alkyl, haloalkyl, cycloalkyl, halogen, cyano, alkoxy, haloalkoxy, amino, alkylamino, dialkylamino or thioalkyl, X is oxygen or sulphur, $R^2$ is a radical from the group of hydrogen, alkyl, haloalkyl, alkoxy, haloalkoxy, alkenyl, alkoxyalkyl, optionally halogen-substituted alkylcarbonyl, optionally halogen-substituted alkoxycarbonyl and optionally halogen-substituted cycloalkylcarbonyl, and $R^3$ is a radical from the group of hydrogen, alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy) alkyl, optionally halogen-substituted alkylthioalkyl, optionally halogen-substituted alkylcarbonylalkyl, optionally halogen-substituted alkylsulphinylalkyl, optionally halogen-substituted alkylsulphonylalkyl, optionally halogen-substituted alkoxycarbonylalkyl, alkoxycarbonylamino optionally alkyl-substituted on the nitrogen, alkynyloxy, alkynyloxycarbonyl, optionally substituted cycloalkyl, optionally substituted cycloalkylcarbonyl, optionally substituted cycloalkylalkyl, optionally substituted heterocyclyl, optionally substituted heterocyclylalkyl, optionally substituted arylalkyl, optionally halogen-substituted arylalkyl, optionally substituted hetarylalkyl and $NR^4R^5$ in which $R^4$ and $R^5$ are each independently a radical from the group of hydrogen, alkyl, haloalkyl, cycloalkyl, alkoxy, alkylcarbonyl, alkoxycarbonyl, hetaryl and heterocyclyl, or $R^4$ and $R^5$ together with the nitrogen atom to which they are bonded form an optionally substituted heterocycle, or $R^2$ and $R^3$ together with the nitrogen atom to which they are bonded form an optionally substituted ring which optionally contains further heteroatoms, and salts and N-oxides of the compounds of the formula (I).

More particularly, the abovementioned problem, and also further objects which are not stated explicitly and are derivable or discernible from the connections discussed herein, are achieved by novel compounds of the abovementioned formula (I), in which G is N, CH, C-halogen, C-nitro, C-cyano, C-alkyl, C-haloalkyl, C-cycloalkyl, C-alkoxy, C-haloalkoxy, $R^1$ is hydrogen, alkyl, haloalkyl, cycloalkyl, halogen, cyano, alkoxy, haloalkoxy, amino, alkylamino, dialkylamino or thioalkyl, X is oxygen or sulphur, $R^2$ is a radical from the group of hydrogen, alkyl, haloalkyl, alkoxy, haloalkoxy, alkenyl, alkoxyalkyl, optionally halogen-substituted alkylcarbonyl, optionally halogen-substituted alkoxycarbonyl and optionally halogen-substituted cycloalkylcarbonyl, and $R^3$ is a radical from the group of hydrogen, alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy) alkyl, optionally halogen-substituted alkylthioalkyl, optionally halogen-substituted alkylcarbonylalkyl, optionally halogen-substituted alkylsulphinylalkyl, optionally halogen-substituted alkylsulphonylalkyl, optionally halogen-substituted alkoxycarbonylalkyl, alkoxycarbonylamino optionally alkyl-substituted on the nitrogen, alkynyloxy, alkynyloxycarbonyl, optionally halogen-, cyano-, alkyl-, haloalkyl-, alkoxy-, haloalkoxy-, alkoxycarbonyl-, haloalkoxycarbonyl- or hetaryl-substituted (where hetaryl may itself be substituted by alkyl or halogen) cycloalkyl, optionally halogen-, cyano-, alkyl-, haloalkyl-, alkoxy-, haloalkoxy-, alkoxycarbonyl-, haloalkoxycarbonyl- or hetaryl-substituted (where hetaryl may itself be substituted by alkyl or halogen) cycloalkylcarbonyl, optionally halogen-, cyano-, alkyl-, haloalkyl-, alkoxy-, haloalkoxy-, alkoxycarbonyl-, haloalkoxycarbonyl- or hetaryl-substituted (where hetaryl may itself be substituted by alkyl or halogen) cycloalkylalkyl, optionally substituted heterocyclyl, optionally halogen-, cyano- (including in the alkyl moiety), nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, cycloalkylalkyl-, alkylcarbonyl-, alkoxycarbonyl- or aminocarbonyl-substituted and optionally benzofused heterocyclylalkyl, optionally halogen-, cyano-, alkyl-, haloalkyl-, alkoxy- or haloalkoxy-substituted arylalkyl, optionally halogen-substituted aryloxyalkyl, optionally halogen-, cyano- (including in the alkyl moiety), nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetarylalkyl and NR$^4$R$^5$ in which R$^4$ and R$^5$ are each independently a radical from the group of hydrogen, alkyl, haloalkyl, cycloalkyl, alkoxy, alkylcarbonyl, alkoxycarbonyl, hetaryl and heterocyclyl, or R$^4$ and R$^5$ together with the nitrogen atom to which they are bonded form an optionally substituted heterocycle, or R$^2$ and R$^3$ together with the nitrogen atom to which they are bonded form an optionally substituted ring which optionally contains further heteroatoms, and salts and N-oxides of the compounds of the formula (I).

Moreover, it has been found that the novel compounds of the formula (I) are obtained when compounds of the formula (II)

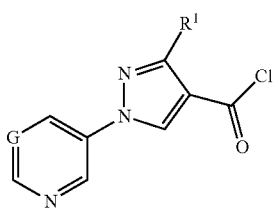

(II)

in which

G and R$^1$ are each as defined above are reacted with compounds of the formula (III)

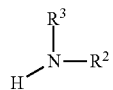

(III)

in which

R$^2$ and R$^3$ are each as defined above, optionally in the presence of a suitable diluent and optionally in the presence of a base.

The compounds of the formula (I), obtainable by these methods in which X is oxygen, can be converted to compounds of the formula (I) by reaction with a sulphurizing reagent in which X is sulphur.

Finally, it has been found that the novel compounds of the formula (I) possess very marked biological properties and are suitable in particular for control of animal pests, especially of insects, arachnids and nematodes, which occur in agriculture, in forests, in protection of stored products and materials, and in the hygiene sector.

Depending on the type of substituents, the compounds of the formula (I) may optionally be present in the form of geometric and/or in the form of optically active isomers or corresponding isomer mixtures in different compositions. The invention relates both to the pure isomers and to the isomer mixtures.

The inventive compounds may also be present in the form of metal complexes, as described for other amides, for example, in DE 2221647.

Preferred substituents and ranges of the radicals listed in the aforementioned compounds of the formula (I) are illustrated hereinafter. The pyrimidyl radical is also referred to as pyrimidinyl, and the furyl radical as furanyl.

G is N, CH, C-halogen, C-nitro, C-cyano, C—C$_1$-C$_6$-alkyl, C—C$_1$-C$_6$-haloalkyl, C—C$_3$-C$_6$-cycloalkyl, C—C$_1$-C$_6$-alkoxy, C—C$_1$-C$_6$-haloalkoxy, especially N, CH, C-halogen, C-cyano, C-trifluoromethyl.

R$^1$ is hydrogen, C$_1$-C$_6$-alkyl, C$_1$-C$_6$-haloalkyl, C$_3$-C$_6$-cycloalkyl, halogen, cyano, C$_1$-C$_6$-alkoxy, C$_1$-C$_6$-haloalkoxy, amino, C$_1$-C$_6$-alkylamino, di(C$_1$-C$_6$)-alkylamino or C$_1$-C$_6$-thioalkyl, especially hydrogen or methyl.

X is oxygen or sulphur.

R$^2$ is a radical from the group of hydrogen, C$_1$-C$_6$-alkyl, C$_1$-C$_6$-haloalkyl, C$_1$-C$_4$-alkoxy, C$_1$-C$_4$-haloalkoxy, C$_2$-C$_4$-alkenyl, C$_1$-C$_4$-alkoxy-C$_1$-C$_4$-alkyl, optionally halogen-substituted C$_1$-C$_4$-alkylcarbonyl, optionally halogen-substituted C$_1$-C$_4$-alkoxycarbonyl and optionally halogen-substituted C$_3$-C$_6$-cycloalkylcarbonyl.

R$^3$ is a radical from the group of hydrogen, C$_1$-C$_6$-alkyl, C$_1$-C$_6$-haloalkyl, cyano-C$_1$-C$_6$-alkyl, C$_2$-C$_4$-alkenyl, C$_2$-C$_4$-haloalkenyl, C$_2$-C$_4$-alkynyl, C$_2$-C$_4$-haloalkynyl, C$_1$-C$_6$-alkoxy, C$_1$-C$_6$-haloalkoxy, optionally halogen-substituted C$_1$-C$_6$-alkoxy-C$_1$-C$_6$-alkyl, optionally halogen-substituted bis(C$_1$-C$_6$-alkoxy)-C$_1$-C$_6$-alkyl, optionally halogen-substituted C$_1$-C$_6$-alkylthio-C$_1$-C$_6$-alkyl, optionally halogen-substituted C$_1$-C$_4$-alkylcarbonyl-C$_1$-C$_4$-alkyl, optionally halogen-substituted C$_1$-C$_6$-alkylsulphinyl-C$_1$-C$_6$-alkyl, optionally halogen-substituted C$_1$-C$_6$-alkylsulphonyl-C$_1$-C$_6$-alkyl, optionally halogen-substituted C$_1$-C$_6$-alkoxycarbonyl-C$_1$-C$_6$-alkyl, C$_1$-C$_6$-alkoxycarbonylamino optionally C$_1$-C$_6$-alkyl-substituted on the nitrogen, C$_2$-C$_4$-alkynyloxy, C$_2$-C$_4$-alkynyloxycarbonyl, optionally halogen-, cyano-, C$_1$-C$_6$-alkyl-, C$_1$-C$_6$-haloalkyl-, C$_1$-C$_6$-alkoxy-, C$_1$-C$_6$-haloalkoxy-, C$_1$-C$_6$-alkoxycarbonyl-, C$_1$-C$_6$-haloalkoxycarbonyl- or hetaryl-substituted (where hetaryl is itself optionally substituted by C$_1$-C$_6$-alkyl or halogen) C$_3$-C$_6$-cycloalkyl, optionally halogen-, cyano-, C$_1$-C$_6$-alkyl-, C$_1$-C$_6$-haloalkyl-, C$_1$-C$_6$-alkoxy-, C$_1$-C$_6$-haloalkoxy-, C$_1$-C$_6$-alkoxycarbonyl-, C$_1$-C$_6$-haloalkoxycarbonyl- or hetaryl-substituted (where hetaryl is itself optionally substituted by C$_1$-C$_6$-alkyl or halogen) C$_3$-C$_6$-cycloalkylcarbonyl, optionally halogen-, cyano-, C$_1$-C$_6$-alkyl-, C$_1$-C$_6$-haloalkyl-, C$_1$-C$_6$-alkoxy-, C$_1$-C$_6$-haloalkoxy-, C$_1$-C$_6$-alkoxycarbonyl-, C$_1$-C$_6$-haloalkoxycarbonyl- or hetaryl-substituted (where hetaryl is itself optionally substituted by C$_1$-C$_6$-alkyl or halogen) C$_3$-C$_6$-cycloalkyl-C$_1$-C$_6$-alkyl, optionally halogen-, cyano- (including in the alkyl moiety), nitro-, C$_1$-C$_6$-alkyl-, C$_1$-C$_6$-haloalkyl-, C$_3$-C$_6$-cycloalkyl-, C$_1$-C$_6$-alkoxy-, C$_1$-C$_6$-haloalkoxy-, C$_1$-C$_6$-alkylthio-, C$_1$-C$_6$-haloalkylthio-, C$_1$-C$_6$-alkylsulphinyl-, C$_1$-C$_6$-alkylsulphonyl-, C$_1$-C$_6$-haloalkylsulphinyl-, C$_1$-C$_6$-haloalkylsulphonyl-, amino-, C$_1$-C$_6$-alkylamino-, di(C$_1$-C$_6$-alkyl)amino-, C$_1$-C$_6$-alkylcarbonyl C$_1$-C$_6$-alkoxycarbonylamino-, C$_1$-C$_6$-alkoxy-C$_1$-C$_6$-alkyl-, C$_1$-C$_6$-haloalkoxy-C$_1$-C$_6$-alkyl-, C$_2$-C$_6$-alkenyl-, C$_2$-C$_6$-alkynyl-, C$_1$-C$_6$-alkyl-C$_3$-C$_6$-cycloalkyl-, C$_3$-C$_6$-cycloalkyl-C$_1$-C$_6$-alkyl-, C$_1$-C$_6$-alkylcarbonyl-, C$_1$-C$_6$-alkoxycarbonyl- or aminocarbonyl-substituted and optionally benzofused heterocyclyl-C$_1$-C$_6$-alkyl, optionally halogen-, cyano-, C$_1$-C$_6$-alkyl-, C$_1$-C$_6$-haloalkyl-, C$_1$-C$_6$-alkoxy- or C$_1$-C$_6$-haloalkoxy-substituted aryl-C$_1$-C$_6$-alkyl, optionally in the aryl moiety, halogen-substituted aryloxy-C$_1$-C$_6$-alkyl, optionally halogen-, cyano- (including in the alkyl moiety), nitro-, C$_1$-C$_6$-alkyl-, C$_1$-C$_6$-haloalkyl-, C$_3$-C$_6$-cycloalkyl-, C$_1$-C$_6$-alkoxy-, C$_1$-C$_6$-haloalkoxy-, C$_1$-C$_6$-alkylthio-, C$_1$-C$_6$-haloalkylthio-, C$_1$-C$_6$-alkylsulphinyl-, C$_1$-C$_6$-alkylsulphonyl-, C$_1$-C$_6$-haloalkylsulphinyl-, C$_1$-C$_6$-haloalkylsulphonyl-, amino-, C$_1$-C$_6$-alkylamino-, di(C$_1$-C$_6$-alkyl)amino-, C$_1$-C$_6$-alkylcarbonylamino-, $C_1$-$C_6$-alkoxycarbonyl amino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl-$C_1$-$C_6$-alkyl, and $NR^4R^5$ in which $R^4$ and $R^5$ are each independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxycarbonyl, or $R^2$ and $R^3$ together with the nitrogen atom to which they are bonded form an optionally $C_1$-$C_6$-alkyl- or $C_1$-$C_6$-alkoxy-substituted 3- to 7-membered ring which optionally contains one or two further heteroatoms from the group of oxygen, nitrogen and sulphur.

Particularly preferred substituents and ranges of the radicals listed in the inventive compounds of the formula (I) are illustrated hereinafter.

G is N, CH, C-halogen, C-nitro, C-cyano, C—$C_1$-$C_4$ alkyl, C—$C_1$-$C_4$-haloalkyl, C—$C_3$-$C_6$-cycloalkyl, C—$C_1$-$C_4$-alkoxy, C—$C_1$-$C_4$-haloalkoxy, especially N, CH, C-halogen, C-cyano or C-trifluoromethyl.

$R^1$ is hydrogen, $C_1$-$C_4$-alkyl, $C_1$-$C_4$-haloalkyl, $C_3$-$C_6$-cycloalkyl, halogen, cyano, $C_1$-$C_4$-alkoxy, $C_1$-$C_4$-haloalkoxy, amino, $C_1$-$C_4$-alkylamino, di($C_1$-$C_4$)-alkylamino or $C_1$-$C_4$-thioalkyl, especially hydrogen or methyl.

X is oxygen or sulphur.

$R^2$ is a radical from the group of hydrogen, $C_1$-$C_4$-alkyl, $C_1$-$C_4$-haloalkyl, $C_1$-$C_4$-alkoxy, $C_2$-$C_3$-alkenyl, $C_1$-$C_2$-alkoxy-$C_1$-$C_2$-alkyl, $C_1$-$C_2$-alkylcarbonyl, $C_1$-$C_2$-alkoxycarbonyl and in each case optionally halogen-substituted cyclopropylcarbonyl, cyclopentylcarbonyl or cyclohexylcarbonyl.

$R^3$ is a radical from the group of hydrogen, $C_1$-$C_4$-alkyl, $C_1$-$C_5$-haloalkyl, cyano-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, optionally halogen-substituted $C_1$-$C_2$-alkoxy-$C_1$-$C_4$-alkyl, optionally halogen-substituted bis($C_1$-$C_2$-alkoxy)-$C_1$-$C_4$-alkyl, optionally halogen-substituted $C_1$-$C_4$-alkylthio-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, optionally halogen-substituted $C_1$-$C_4$-alkoxycarbonyl-$C_1$-$C_4$-alkyl, $C_1$-$C_4$-alkoxycarbonylamino optionally $C_1$-$C_4$-alkyl-substituted on the nitrogen, $C_2$-$C_4$-alkynyloxy, $C_2$-$C_4$-alkynyloxycarbonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (where pyridyl is itself optionally substituted by $C_1$-$C_4$-alkyl or halogen) $C_3$-$C_6$-cycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (where pyridyl is itself optionally substituted by $C_1$-$C_4$-alkyl or halogen) $C_3$-$C_6$-cycloalkylcarbonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (where pyridyl is itself optionally substituted by $C_1$-$C_4$-alkyl or halogen) $C_3$-$C_6$-cycloalkyl-$C_1$-$C_4$-alkyl, optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted and optionally benzofused heterocyclyl-$C_1$-$C_4$-alkyl, optionally halogen-, cyano-, $C_1$-$C_4$-alkyl-, $C_1$-$C_4$-haloalkyl-, $C_1$-$C_4$-alkoxy- or $C_1$-$C_4$-haloalkoxy-substituted aryl-$C_1$-$C_4$-alkyl, aryloxy-$C_1$-$C_4$-alkyl optionally halogen-substituted in the aryl moiety, optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl-$C_1$-$C_4$-alkyl or $R^2$ and $R^3$ together with the nitrogen atom to which they are bonded form an optionally $C_1$-$C_4$-alkyl- or $C_1$-$C_4$-alkoxy-substituted 3- to 7-membered ring which optionally contains one or two further heteroatoms from the group of oxygen, nitrogen and sulphur, $R^2$ and $R^3$ together are, for example, $CH_2CH_2CH_2$ or $CH_2CH_2CH_2O$.

Very particularly preferred substituents and ranges of the radicals listed in the inventive compounds of the formula (I) are illustrated hereinafter.

G is N, CH, C-halogen, C-cyano, C—$CH_3$, C—$CF_3$, C-cyclopropyl, C—$OCH_3$, C—$OCF_3$, especially N, CH, C-halogen.

$R^1$ is hydrogen, methyl, trifluoromethyl, cyclopropyl, halogen, cyano, methoxy, trifluoromethoxy, amino, methylamino, dimethylamino, especially hydrogen or methyl.

X is oxygen or sulphur.

$R^2$ is a radical from the group of hydrogen, methyl, ethyl, $CH_2CF_3$, $CH_2CF_2CH_3$, $CH_2CHF_2$, $CH_2CF_2CHF_2$, $CH_2CH_2F$, $CH_2$—$CHFCH_3$, $CH_2CF_2Br$, $CH_2CFCl_2$, $CH(CH_3)CH_2F$, $CH_2CCl_3$, $CH_2CClF_2$, $CH_2CH_2CH_2F$, $CH_2CH(CH_3)Cl$, $CHCF_3CH(CH_3)_2$, $CH(CF_3)_2$, $CH_2CH_2Cl$, $CHCF_3CH_2CH_2CH_3$, $CH_2CF_2CF_3$, methoxy, ethoxy, vinyl, $CH_2OCH_3$, $CH_2OCH_2CH_3$, methylcarbonyl, ethylcarbonyl, methoxycarbonyl, ethoxycarbonyl, cyclopropylcarbonyl and fluorocyclopropylcarbonyl.

$R^3$ is a radical from the group of hydrogen, methyl, ethyl, $CH_2CF_3$, $CH_2CH_2CF_3$, $CH_2CF_2CH_3$, $CH_2CHF_2$, $CH_2CF_2CHF_2$, $CH_2CH_2F$, $CH_2$—$CHFCH_3$, $CH_2CF_2Br$, $CH_2CFCl_2$, $CH(CH_3)CH_2F$, $CH_2CCl_3$, $CH_2CClF_2$, $CH_2CH_2CH_2F$, $CH_2CH(CH_3)Cl$, $CHCF_3CH(CH_3)_2$, CH(CF₃)₂, CH₂CH₂Cl, CHCF₃CH₂CH₂CH₃, CH₂CF₂CF₃, C(CH₃)₂CN, CH(CN)CH(CH₃)₂, CH₂CN, CH₂CH₂CN, vinyl, C(CH₃)₂CCH, CH₂CCCH₃, methoxy, ethoxy, CH₂CH(OCH₃)₂, CH₂CH(CH₃)(OCH₃), CH₂C(CH₃)₂(OCH₃), CH(CH₃)CH(OCH₃)₂, CH₂C(CH₃)(OCH₃)₂, C(CH₃)₂—CH₂SCH₃, CH₂CH₂SCH₃, CHCH₃CH₂SCH₃, optionally halogen-substituted C₁-C₄-alkylcarbonyl-C₁-C₄-alkyl, CH₃SO₂CH₂C(CH₃)₂, CH₃SO₂CH₂CHCH₃, propargyloxy, cyclopropyl, cyanocyclopropyl, fluorocyclopropyl, trifluoromethylcyclopropyl, trifluoromethylcyclohexyl, methoxycarbonylcyclopropyl, fluorocyclopropylcarbonyl, cyclopropylmethyl, 1-cyclopropylethyl, cyclohexylmethyl, 1-cyano-1-cyclopropyleth-1-yl, 1,3-dioxolan-2-ylmethyl, 4-methyl-1,3-dioxolan-2-ylmethyl, tetrahydrofurylmethyl, tetrahydropyranylmethyl, 2,2-dimethyl-1,3-dioxolan-5-ylmethyl, 2-methyltetrahydrofur-2-ylmethyl, α-methyl-3,5-dimethyltriazol-1-yl-ethyl, 1,5-dimethyl-1,3-oxazol-4-ylmethyl, optionally halogen-, cyano-, methyl-, ethyl-, methoxy- or ethoxy-substituted benzyl or optionally halogen-, cyano-, methyl-, methoxy- or ethoxy-substituted pyrimidylmethyl, (especially pyrimid-2-ylmethyl, α-methyl-pyrimidylmethyl, 4-bromopyrimid-2-ylmethyl, 2-methylpyrimid-4-ylmethyl, 4,6-dimethylpyrimid-2-ylmethyl, 4-iodopyrimid-2-ylmethyl, 2-ethylpyrimid-6-ylmethyl, 5-chloropyrimid-2-ylmethyl, 5-bromopyrimid-2-ylmethyl, 5-cyanopyrimid-2-ylmethyl, 4,6-dimethoxypyrimid-2-ylmethyl and 4,6-diethoxy-2-pyrimid-2-ylmethyl), oxadiazolylmethyl, oxazolylmethyl, 5-methylpyrazin-2-yl, α-methylpyrid-2-ylmethyl, imidazolylmethyl, 6-chloropyridin-3-ylmethyl, thiazolylmethyl, furanylmethyl, 1,5-dimethylpyrazol-3-ylmethyl, 3-cyclopropyl-1,2,4-oxadiazol-5-ylmethyl, 6-bromopyrid-2-ylmethyl, (2,3-dihydro-1-benzofur-2-yl)methyl, (1,4-dioxan-2-yl)methyl, 1,3-dioxolan-2-ylmethyl, methoxycarbonylethyl (methylalaninate), methoxycarbonylamino, 4,6-dimethoxypyrimid-2-ylmethyl, 2-(2,5-dichlorophenoxy)ethyl and N-methyl-N-methoxycarbonylamino, or $R^2$ and $R^3$ together with the nitrogen atom to which they are bonded form an optionally C₁-C₄-alkyl- or C₁-C₄-alkoxy-substituted 3- to 7-membered ring which optionally contains one or two further heteroatoms from the group of oxygen, nitrogen and sulphur; for example, $R^2$ and $R^3$ together are CH₂CH₂CH₂ or CH₂CH₂CH₂O.

In the preferred definitions, unless stated otherwise, halogen (or halo) is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl and is in turn preferably phenyl, hetaryl (including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, (for example, 1,3-oxazol-4-yl) isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, heterocyclyl (including as part of a larger unit, for example heterocyclylalkyl) is selected from the group of 2-tetrahydrofuranyl, 3-tetrahydrofuranyl, 2,3-dihydro-1-benzofur-2-yl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 1,4-dioxan-2-yl, 1,3-dioxolan-2-yl, 1,3-dioxolan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl.

In the particularly preferred definitions, unless stated otherwise, halogen (or halo) is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl and is in turn preferably phenyl, hetaryl (including as part of a larger unit, for example hetarylalkyl) is selected from the group of pyrimidyl, oxadiazolyl, oxazolyl, pyrazinyl, imidazolyl, thiazolyl and furanyl, heterocyclyl (including as part of a larger unit, for example heterocyclylalkyl) is selected from the group of 2-tetrahydrofuranyl, 3-tetrahydrofuranyl, 2,3-dihydro-1-benzofur-2-yl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 1,4-dioxan-2-yl, 1,3-dioxolan-2-yl, 1,3-dioxolan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl.

Halogen-substituted radicals, e.g. haloalkyl (in expressions such as "haloalkyl,", "halo" has the same meaning as "halogen"), are mono- or polyhalogenated up to the maximum possible number of substituents. In the case of polyhalogenation, the halogen atoms may be the same or different.

Halogen represents fluorine, chlorine, bromine and iodine, especially fluorine, chlorine and bromine.

Preference, particular preference or very particular preference is given to compounds which in each case bear the substituents specified under preferred, particularly preferred or very particularly preferred.

Saturated or unsaturated hydrocarbon radicals such as alkyl or alkenyl may, also in conjunction with heteroatoms, as, for example, in alkoxy, as far as possible, in each case be straight-chain or branched.

Optionally substituted radicals may be mono- or polysubstituted, where the substituents may be the same or different in the case of polysubstitutions.

The radical definitions and illustrations listed above, in general or within preferred ranges, apply correspondingly to the end products and to the starting materials and intermediates. These radical definitions can be combined with one another as desired, i.e. including between the individual preferred ranges.

Preference is given in accordance with the invention to compounds of the formula (I) in which a combination of the definitions listed above as preferred is present.

Particular preference is given in accordance with the invention to compounds of the formula (I) in which a combination of the definitions listed above as particularly preferred is present.

Very particular preference is given in accordance with the invention to compounds of the formula (I) in which a combination of the definitions listed above as very particularly preferred is present.

In an emphasized group of inventive compounds G is CH.

In a further emphasized group of inventive compounds, $R^3$ is haloalkyl.

In a further emphasized group of inventive compounds, $R^3$ is optionally substituted heterocyclylalkyl.

In a further emphasized group of inventive compounds, $R^3$ is optionally substituted hetarylalkyl.

In a further emphasized group of inventive compounds, X is oxygen.

In a further emphasized group of inventive compounds, X is sulphur.

The preparation of inventive compounds of the formula (I) and of corresponding precursors, is illustrated in the following reaction schemes.

Reaction Scheme 1

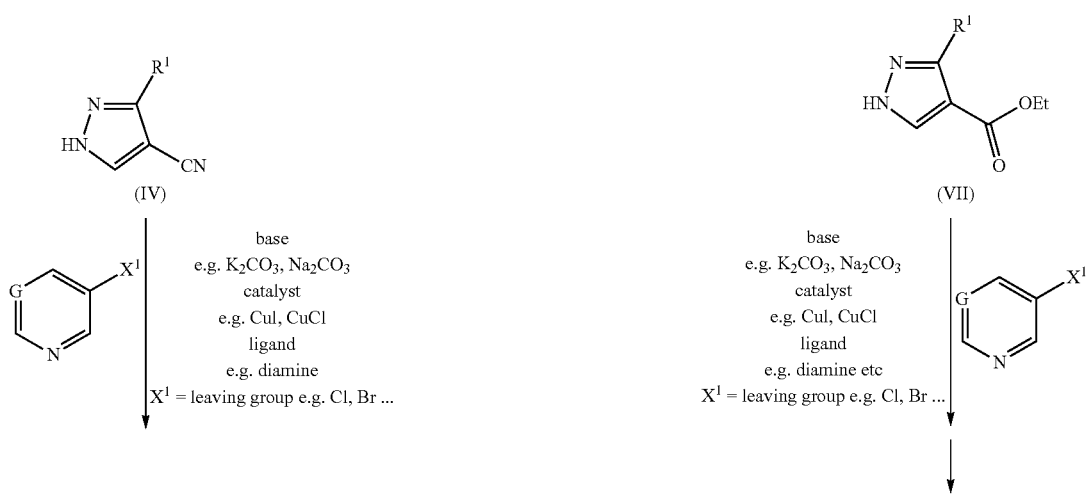

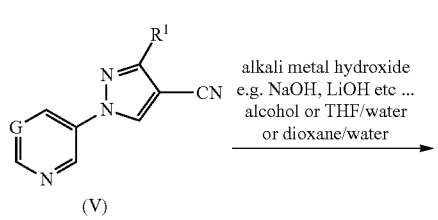
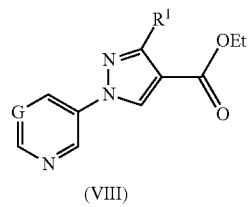
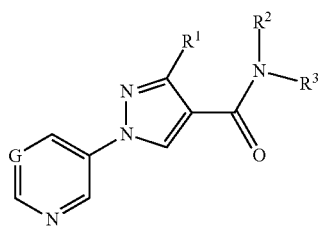
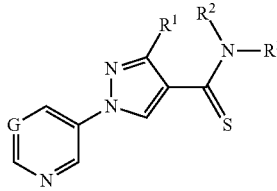

The nitriles of the formula (V) which are required as starting materials, are known or obtainable by known methods, for example as described, when G is CH and R¹ is H, in Journal of Heterocyclic Chemistry 1981, 18, 9-14. The nitriles of the formula (V) can be obtained by N-arylating the pyrazoles (IV) with 3-bromopyridine. The esters of the formula (VIII) required as starting materials are likewise known or obtainable by known methods, for example as described, when G is CH and R¹ is H, in Journal of Organic Chemistry 2004, 69, 5578-5587. Further starting materials of the formulae (V) and (VIII) in which G and R¹ are each as defined above can be prepared by analogous methods.

The pyrazoles of the formulae (V) and (VIII) can be converted using the standard methods specified in Reaction Scheme 1 (cf., for example, DE 2221647), first to the acids of the formula (VI) and then to the acid chlorides of the formula (II). Further reaction with the amines of the formula (III) in which R² and R³ are each as defined above, in a diluent, for example dichloromethane or tetrahydrofuran and in the presence of a base, for example triethylamine or diisopropylethylamine, leads to inventive compounds of the formula (I).

The compounds of the formula (I) can be prepared directly from the acids of the formula (VI) by reaction with amines of the formula (III) in the presence of coupling agents, for example EDC (1-ethyl-3-[3-dimethylaminopropyl]carbodiimide hydrochloride), DCC (dicyclohexylcarbodiimide) or BoPCl (bis(2-oxo-3-oxazolidinyl)phosphinic chloride).

Reaction Scheme 2

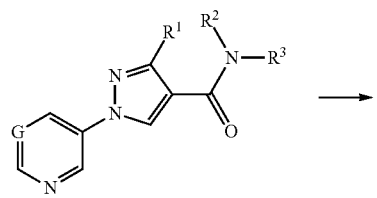

The conversion of amides to thioamides can be carried out with P₄S₁₀ or Lawesson's reagent.

For reactions with Lawesson's reagent, see: Bull. Soc. Chem. Bel. 1978, 87, 223.

The inventive active ingredients, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus mactans, Metatetranychus* spp., *Nuphersa* spp., *Oligonychus* spp., *Ornithodoros* spp., *Panonychus* spp., *Phyllo-*

*coptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Prenmotrypes* spp., *Psylliodes* spp., *Ptinus* spp., *Rhizobius ventralis, Rhizopertha dominica, Sitophilus* spp., *Sphenophorus* spp., *Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Diplopoda, for example, *Blaniulus guttulatus.*

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Cochliomyia* spp., *Contarinia* spp., *Cordylobia anthropophaga, Culex* spp., *Cuterebra* spp., *Dacus oleae, Dasyneura* spp., *Delia* spp., *Dermatobia hominis, Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit, Pegomyia* spp., *Phorbia* spp., *Prodiplosis* spp., *Psila rosae, Rhagoletis* spp., *Stomoxys* spp., *Tabanus* spp., *Tannia* spp., *Tetanops* spp., *Tipula* spp.

From the class of the Gastropoda, for example, *Anon* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example, *Athalia* spp., *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Acromyrmex* spp., *Atta* spp., *Cornitermes cumulans, Microtermes obesi, Odontotermes* spp., *Reticulitermes* spp.

From the order of the Lepidoptera, for example, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia kuehniella*, *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthedon* spp., *Tecia solanivora*, *Thermesia gemmatalis*, *Tinea pellionella*, *Tineola bisselliella*, *Tortrix* spp., *Trichoplusia* spp., *Tuta absoluta*, *Virachola* spp.

From the order of the Orthoptera, for example, *Acheta domesticus*, *Blatta orientalis*, *Blattella germanica*, *Dichroplus* spp., *Dichroplus* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella* spp.

From the order of the Thysanoptera, for example, *Anaphothrips obscurus*, *Baliothrips biformis*, *Drepanothris reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis*, *Trichodorus* spp., *Tylenchulus semipenetrans*, *Xiphinema* spp.

The inventive compounds can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). They can also be employed as intermediates or precursors for the synthesis of other active ingredients.

The active ingredients can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active ingredient, synthetic materials impregnated with active ingredient, fertilizers and microencapsulations in polymeric substances.

These formulations are produced in a known manner, for example by mixing the active ingredients with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose, natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active ingredient, preferably between 0.5 and 90%.

The inventive active ingredients may be used as they are or in their formulations, including a mixture with one or more suitable fungicides, bactericides, acaricides, nematicides, insecticides, microbiologicals, fertilizers, attractants, sterilants, synergists, safeners, semiochemicals and/or plant growth regulators, in order thereby, for example, to broaden the activity spectrum, to prolong the duration of action, to increase the rate of action, to prevent repulsion or to prevent development of resistance. Furthermore, combinations of this kind may improve plant growth, raise tolerance towards abiotic factors such as high or low temperatures, against drought or against increased levels of water and/or soil salt. It is also possible to improve the flowering and fruiting performance, to facilitate harvesting and increase yields, to influence ripening, to increase the quality and/or nutritional value of the harvested products, to prolong storage life and/or to improve the manageability of the harvested products. Generally speaking, combining the active ingredients of the invention and co-components produces synergistic effects—that is, the activity of the mixture in question is greater than the activity of the individual components. In general it is possible to use the combinations not only in premixes, tankmixes or ready-made mixes but also in seed applications.

Particularly favourable co-components are, for example, those listed below.

Insecticides/Acaricides/Nematicides:

The active ingredients identified here by their common name are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors, for example
carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example
organochlorines, for example chlordane and endosulfan (alpha-); or
fiproles (phenylpyrazoles), for example ethiprole, fipronil, pyrafluprole and pyriprole.

(3) Sodium channel modulators/voltage-dependent sodium channel blockers, for example
pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, pelinethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or
DDT; or methoxychlor.

(4) Nicotinergic acetylcholine receptor agonists, for example
neonicotinoids, for example acetamiprid, clothianidin, dinotefuran, imidacloprid, nitenpyram, thiacloprid, thiamethoxam; or
nicotine.

(5) Allosteric acetylcholine receptor modulators (agonists), for example
spinosyns, for example spinetoram and spinosad.

(6) Chloride channel activators, for example
avermectins/milbemycins, for example abamectin, emamectin benzoate, lepimectin and milbemectin.

(7) Juvenile hormone analogues, for example hydroprene, kinoprene, methoprene; or fenoxycarb; pyriproxyfen.

(8) Active ingredients with unknown or non-specific mechanisms of action, for example
fumigants, for example methyl bromide and other alkyl halides; or
chloropicrin; sulphuryl fluoride; borax; tartar emetic.

(9) Selective antifeedants, for example pymetrozine; or flonicamid.

(10) Mite growth inhibitors, for example clofentezine, diflovidazin, hexythiazox, etoxazole.

(11) Microbial disruptors of the insect gut membrane, for example *Bacillus thuringiensis* subspecies *israelensis, Bacillus sphaericus, Bacillus thuringiensis* subspecies *aizawai, Bacillus thuringiensis subspecies kurstaki, Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron; or organotin compounds, for example azocyclotin, cyhexatin, fenbutatin oxide; or propargite; tetradifon.

(13) Oxidative phoshorylation decouplers acting by interrupting the H proton gradient, for example chlorfenapyr and DNOC.

(14) Nicotinergic acetylcholine receptor antagonists, for example bensultap, cartap (hydrochloride), thiocylam, and thiosultap (sodium).

(15) Chitin biosynthesis inhibitors, type 0, for example benzoylureas, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting disruptors, for example cyromazine.

(18) Ecdysone agonists/disruptors, for example
diacylhydrazines, for example chromafenozide, halofenozide, methoxyfenozide and tebufenozide.

(19) Octopaminergic agonists, for example amitraz.

(20) Complex-III electron transport inhibitors, for example hydramethylnone; acequinocyl; fluacrypyrim.

(21) Complex-I electron transport inhibitors, for example from the group of the METI acaricides, for example fenazaquin, fenpyroximate, pyrimidifen, pyridaben, tebufenpyrad, tolfenpyrad; or rotenone (Denis).

(22) Voltage-dependent sodium channel blockers, for example indoxacarb; metaflumizone.

(23) Inhibitors of acetyl-CoA carboxylase, for example tetronic acid derivatives, for example spirodiclofen and spiromesifen; or tetramic acid derivatives, for example spirotetramat.

(24) Complex-IV electron transport inhibitors, for example phosphines, for example aluminium phosphide, calcium phosphide, phosphine, zinc phosphide; or cyanide.

(25) Complex-II electron transport inhibitors, for example cyenopyrafen.

(28) Ryanodine receptor effectors, for example diamides, for example flubendiamide, chlorantraniliprole (Rynaxypyr), cyantraniliprole (Cyazypyr) and also 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazine-carboxylate (known from WO2007/043677).

Further active ingredients with unknown mechanism of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, pyridalyl and pyrifluquinazon; and also products based on *Bacillus firmus* (I-1582, BioNeem, Votivo) and also the known active ingredients below 4-{[(6-bromopyrid-3-yl)methyl](2-fluoroethyl)amino}furan-2(5H)-one (known from WO 2007/115644),
4-{[(6-fluoropyrid-3-yl)methyl](2,2-difluoroethyl)amino}furan-2(5H)-one (known from WO 2007/115644),
4-{[(2-chloro-1,3-thiazol-5-yl)methyl](2-fluoroethyl)amino}furan-2(5H)-one (known from WO 2007/115644),
4-{[(6-chloropyrid-3-yl)methyl](2-fluoroethyl)amino}furan-2(5H)-one (known from WO 2007/115644),
4-{[(6-chloropyrid-3-yl)methyl](2,2-difluoroethyl)amino}furan-2(5H)-one (known from WO 2007/115644),
4-{[(6-chloro-5-fluoropyrid-3-yl)methyl](methyl)amino}furan-2(5H)-one (known from WO 2007/115643),
4-{[(5,6-dichloropyrid-3-yl)methyl](2-fluoroethyl)amino}furan-2(5H)-one (known from WO 2007/115646),
4-{[(6-chloro-5-fluoropyrid-3-yl)methyl](cyclopropyl)amino}furan-2(5H)-one (known from WO 2007/115643),
4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-$\lambda^4$-sulphanylidenecyanamide (known from WO 2007/149134), [1-(6-chloropyridin-3-yl)ethyl](methyl)oxido-$\lambda^4$-sulphanylidenecyanamide (known from WO 2007/149134) and its diastereomers (A) and (B)

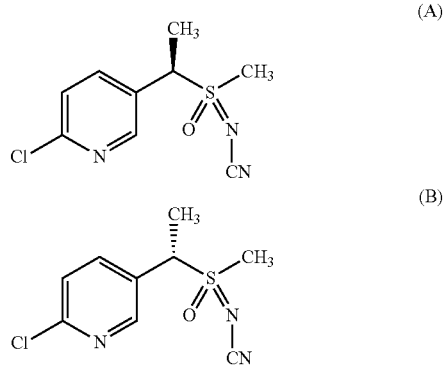

(also known from WO 2007/149134), [(6-trifluoromethylpyridin-3-yl)methyl](methyl)oxido-$\lambda^4$-sulphanylidenecyanamide (known from WO 2007/095229), sulfoxaflor (known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-[2-fluoro-4-methyl-5-[(2,2,2-trifluoroethyl)sulphinyl]phenyl]-3-(trifluoromethyl)-1H-1,2,4-triazole-5-amine (known from WO 2006/043635),

[(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-1)]chromen-4-yl]methyl cyclopropanecarboxylate (known from WO 2006/129714), 2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288), 2-cyano-3-(difluoromethoxy)-N-ethylbenzenesulphonamide (known from WO2005/035486), 4-(difluoromethoxy)-N-ethyl-N-methyl-1,2-benzothiazole-3-amine 1,1-dioxide (known from WO2007/057407) and N-[1-(2,3-dimethylphenyl)-2-(3,5-dimethylphenyl)ethyl]-4,5-dihydro-1,3-thiazole-2-amine (known from WO2008/104503).

In a preferred embodiment of the invention, a penetrant is additionally added to the crop protection compositions to enhance the action. Examples of useful penetrants also include substances which promote the availability of the compounds of the formula (I) in the spray coating. These include, for example, mineral or vegetable oils. Useful oils include all mineral or vegetable oils—modified or otherwise—which are typically usable in agrochemical compositions. Examples include sunflower oil, rapeseed oil, olive oil, castor oil, colza oil, cornseed oil, cottonseed oil and soya oil or the esters of the oils mentioned. Preference is given to rapeseed oil, sunflower oil and their methyl or ethyl esters, especially rapeseed oil methyl ester.

The concentration of penetrants in the compositions of the invention can be varied within a wide range. In the case of a formulated crop protection composition, it is generally 1 to 95% by weight, preferably 1 to 55% by weight, more preferably 15-40% by weight. In the ready-to-use compositions (spray liquors), the concentrations are generally between 0.1 and 10 g/l, preferably between 0.5 and 5 g/l.

When used as insecticides, the inventive active ingredients can furthermore be present in their commercially available formulations and in the use forms, prepared from these formulations, as a mixture with synergists. Synergists are compounds which increase the action of the active ingredients, without it being necessary for the synergistic agent added to be active itself.

When used as insecticides, the inventive active ingredients can furthermore be present in their commercially available formulations and in the use forms, prepared from these formulations, as mixtures with inhibitors which reduce degradation of the active ingredient after use in the environment of the plant, on the surface of parts of plants or in plant tissues.

The active ingredient content of the use fours prepared from the commercially available formulations can vary within wide limits. The active ingredient concentration of the use forms can be from 0.00000001 to 95% by weight of active ingredient, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Examples include the important crop plants such as cereals (wheat, rice), maize, soya, potatoes, sugar beet, tomatoes, peas and other vegetable varieties, cotton, tobacco, oilseed rape, and also fruit plants (the fruits being apples, peas, citrus fruits and grapes). Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Inventive treatment of the plants and plant parts with the active ingredients is carried out directly or by allowing the compounds to act on the surroundings, habitat or storage space by the customary treatment methods, for example by immersion, spraying, evaporation, fogging, scattering, painting on, injecting and, in the case of propagation material, in particular in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated in accordance with the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment in accordance with the invention may also result in superadditive ("synergistic") effects. Thus, for example, reduced application rates and/or a widening of the activity spectrum and/or an increase in the activity of the substances and compositions which can be used in accordance with the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processibility of the harvested products are possible, which exceed the effects which were actually to be expected.

The transgenic plants or plant cultivars (obtained by genetic engineering) which are preferably to be treated in accordance with the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering and fruiting performance, easier harvesting, accelerated maturation, higher harvest yields, higher quality and/or a higher nutritional value of the harvested products, better storage stability and/or processibility of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active ingredients. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA (b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active ingredients, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), Knock-Out® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated in accordance with the invention in a particularly advantageous manner with the compounds of the general formula (I) and/or the inventive active ingredient mixtures. The preferred ranges stated above for the active ingredients or mixtures also apply to the treatment of these plants. Particular emphasis is given to the treatment of plants with the compounds or mixtures specifically mentioned in the present text.

The inventive active ingredients act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp. (*Ctenocephalides canis*, *Ctenocephalides felis*), *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis*, *Periplaneta americana*, *Blattela germanica*, *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The inventive active ingredients of the formula (I) are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the inventive active ingredients.

The inventive active ingredients are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal application, by dermal use in the form, for example, of dipping or bathing, spraying, pouring on and spotting on, washing and powdering, and also with the aid of moulded articles containing the active ingredient, such as collars, ear marks, tail marks, limb bands, halters, marking devices and the like.

When used for cattle, poultry, pets and the like, the active ingredients of the formula (I) can be used as formulations (for example powders, emulsions, free-flowing compositions), which comprise the active ingredients in an amount of from 1 to 80% by weight, directly or after 100 to 10 000-fold dilution, or they can be used as a chemical bath.

It has furthermore been found that the inventive compounds also have a strong insecticidal action against insects which destroy industrial materials.

The following insects may be mentioned as examples and as preferred—but without any limitation:

beetles, such as *Hylotrupes bajulus*, *Chlorophorus pilosis*, *Anobium punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *Heterobostrychus brunneus*, *Sinoxylon* spec. *Dinoderus minutus*;

hymenopterons, such as *Sirex juvencus*, *Urocerus gigas*, *Urocerus gigas taignus*, *Urocerus augur*;

termites, such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis*, *Coptotermes formosanus*;

bristletails, such as *Lepisma saccharina*.

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The inventive compounds can likewise be employed for protecting objects which come into contact with saltwater or brackish water, in particular hulls, screens, nets, buildings, moorings and signalling systems, against fouling.

Furthermore, the inventive compounds, alone or in combinations with other active ingredients, may be employed as antifouling agents.

In domestic, hygiene and stored-product protection, the active ingredients are also suitable for controlling animal pests, in particular insects, arachnids and mites, which are found in enclosed spaces such as, for example, dwellings, factory halls, offices, vehicle cabins and the like. They can be employed alone or in combination with other active ingredients and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp.*, Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella gemianica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of domestic insecticides, they are used alone or in combination with other suitable active ingredients, such as phosphoric esters, carbamates, pyrethroids, neonicotinoids, growth regulators or active ingredients from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for scattering or in bait stations.

PREPARATION EXAMPLES

Example A

Stage 1: 1-(Pyridin-3-yl)-1H-pyrazole-4-carbonitrile

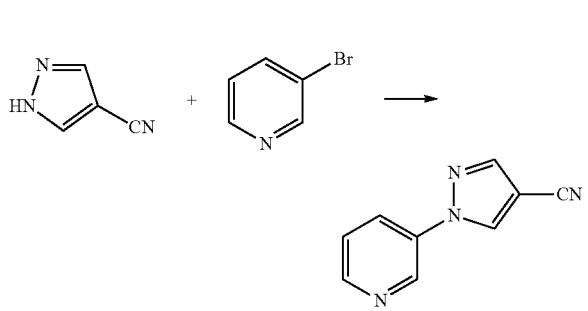 [SMILES: N#Cc1cn[nH]c1 ; Brc1cccnc1 ; N#Cc1cnn(-c2cccnc2)c1]

1.559 g (11.28 mmol) of potassium carbonate, 0.051 g (0.269 mmol) of copper iodide, 0.153 g (1.074 mmol) of trans-N,N'-dimethyl-1,2-cyclohexanediamine and 0.500 g (5.371 mmol) of 4-cyanopyrazole were dissolved under argon in 2.07 ml (21.49 mmol) of 3-bromopyridine. The mixture was heated to 110° C. for 24 h and then cooled to room temperature. Dichloromethane was added and the solids were filtered off. The filtrate was concentrated and the residue was stirred with diethyl ether. The precipitate formed was filtered off and dried on a rotary evaporator.

Yield: 0.710 mg (78% of theory), log P[1)] (HCOOH) 0.98
$^1$H NMR((CD$_3$)$_2$SO): 7.59 (m, 1H), 8.24 (m, 1H), 8.36 (s, 1H), 8.63 (m, 1H), 9.09 (m, 1H), 9.33 (s, 1H)

Stage 2: 1-(Pyridin-3-yl)-1H-pyrazole-4-carboxylic acid

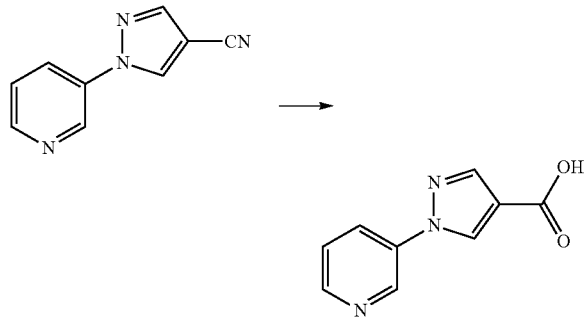 [SMILES: N#Cc1cnn(-c2cccnc2)c1 ; O=C(O)c1cnn(-c2cccnc2)c1]

8.360 g (49.13 mmol) of 1-(pyridin-3-yl)-1H-pyrazole-4-carbonitrile were dissolved in approx. 200 ml of dioxane and admixed with approx. 15 ml of water and 10.48 g of 45% aqueous sodium hydroxide solution. The mixture was heated under reflux for 12 h. Since the conversion was incomplete, an additional 10.48 g of a 45% aqueous sodium hydroxide solution were added, and the mixture was once again heated under reflux for 12 h. The solution was cooled to room temperature and the dioxane was removed under reduced pressure. The residue was admixed with a little water and extracted with ethyl acetate. The aqueous phase was adjusted to pH 3 at 0° C. with conc. HCl and the precipitate formed was filtered off; this gave 5.04 g. The filtrate was concentrated by half and the solid which precipitates was filtered off with suction; a further 2.29 g were isolated in this way.

Yield: 7.33 g (72% of theory), log P[1)] (HCOOH) 0.50
$^1$H NMR((CD$_3$)$_2$SO): 7.55 (m, 1H), 8.08 (s, 1H), 8.28 (m, 1H), 8.57 (m, 1H), 8.98 (s, 1H), 9.13 (m, 1H)

Stage 3: (Pyridin-3-yl)-1H-pyrazole-4-carbonyl chloride hydrochloride

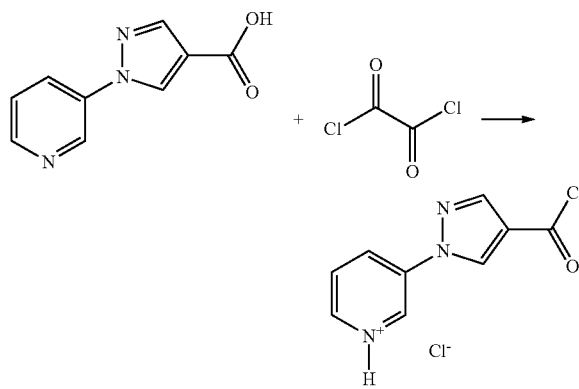

4.00 g (21.15 mmol) of 1-(pyridin-3-yl)-1H-pyrazole-4-carboxylic acid were initially charged in approx. 100 ml of dichloromethane, and admixed with 2 drops of dimethylformamide under argon. 7.783 g (61.32 mmol) of oxalyl chloride were added dropwise and, after the end of the addition, the mixture was stirred at room temperature for 1 hour. The solution was concentrated, and the residue was admixed with approx. 10 ml of toluene and concentrated. This gave a colourless solid which was converted further immediately.

Stage 4: N-Ethyl-1-(pyridin-3-yl)-1H-pyrazole-4-carboxamide

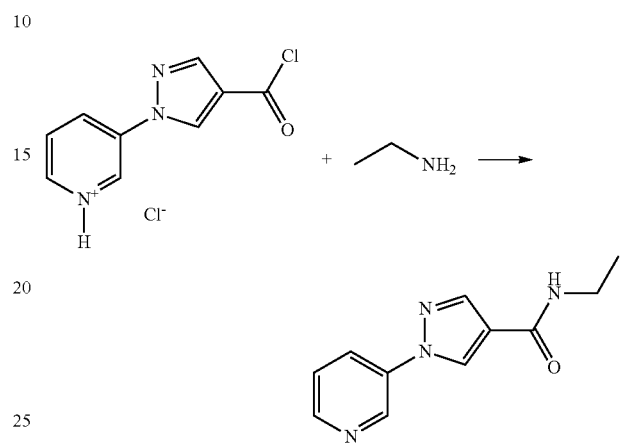

0.109 g (2.408 mmol) of ethylamine were dissolved in 20 ml of dioxane, and 0.934 g (7.225 mmol) of N,N-diisopropylethylamine were added dropwise under argon. A solution of 0.500 g (2.408 mmol) of crude product from the preceding stage in approx. 40 ml of dioxane was added (slightly exothermic). The mixture was stirred at room temperature for 12 hours and then concentrated. The residue was admixed with ethyl acetate/water, and the aqueous phase was extracted with ethyl acetate. The organic phase was dried with magnesium sulphate, then concentrated and stirred with diethyl ether. The solids were filtered off.

Yield: 0.240 g (46% of theory), log P[1)] (HCOOH) 0.64
$^1$H NMR((CD$_3$)$_2$SO): 1.13 (t, 3H), 3.28 (q, 2H), 7.56 (m, 1H), 8.03 (NH, 1H), 8.15 (s, 1H), 8.21 (m, 1H), 8.55 (m, 1H), 8.90 (s, 1H), 9.08 (m, 1H)

Example B

Stage 1: Ethyl 3-methyl-1-(pyridin-3-yl)-1H-pyrazole-4-carboxylate

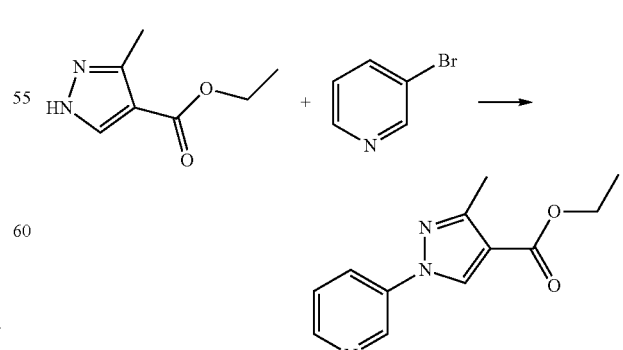

3.765 g (27.24 mmol) of potassium carbonate, 0.124 g (0.649 mmol) of copper iodide, 0.296 g (2.595 mmol) of trans-N,N'-dimethyl-1,2-cyclohexanediamine and 2.000 g (12.97 mmol) of ethyl 3-methylpyrazole-4-carboxylate were dissolved in 5.0 ml (51.90 mmol) of 3-bromopyridine under argon. The mixture was heated to 110° C. for 24 hours and then cooled to room temperature. Dichloromethane was added and the solids were filtered off. The filtrate was concentrated and the residue was purified by chromatography on silica gel (cyclohexane/ethyl acetate, 4:1).

Yield: 2.18 g (73% of theory), log P[1)] (HCOOH) 1.83. Contains 13% regioisomer (log P[1)] (HCOOH) 1.63).

$^1$H NMR((CD$_3$)$_2$SO): 1.31 (t, 3H), 2.46 (s, 3H), 4.27 (q, 2H), 7.53 (m, 1H), 8.26 (m, 1H), 8.55 (m, 1H), 8.96 (s, 1H), 9.11 (m, 1H)

Stage 2: 3-Methyl-1-(pyridin-3-yl)-1H-pyrazole-4-carboxylic acid

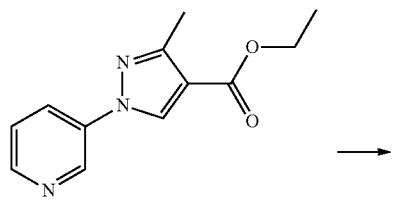

2.180 g (9.427 mmol) of ethyl 3-methyl-1-(pyridin-3-yl)-1H-pyrazole-4-carboxylate (contaminated with approx. 10% regioisomer) was dissolved in approx. 50 ml of dioxane, and admixed with approx. 15 ml of water and 2.011 g of a 45% aqueous sodium hydroxide solution. The mixture was stirred at room temperature for 12 h. Since the conversion was incomplete, the reaction mixture was additionally heated under reflux for 5 h. The solution was cooled to room temperature and the dioxane was removed under reduced pressure. The residue was admixed with water and extracted with ethyl acetate. The organic phase was discarded and the aqueous phase was adjusted to pH 3 at 0° C. with 1N HCl and extracted with ethyl acetate. The organic phase was dried with magnesium sulphate and concentrated. This gave 1.56 g of the desired acid. After 12 h, a solid had precipitated out in the aqueous phase; it was filtered off with suction and gave 0.090 g of additional product.

Yield: 1.65 g (86% of theory), log P[31)] (HCOOH) 0.77. The sample contains 9% regioisomer (log P[1)] (HCOOH) 0.53).

[1]NMR((CD$_3$)$_2$SO): 2.45 (s, 3H), 7.52 (m, 1H), 8.23 (m, 1H), 8.53 (m, 1H), 8.91 (s, 1H), 9.01 (m, 1H)

Stage 3: 3-Methyl-1-(pyridin-3-yl)-1H-pyrazole-4-carbonyl chloride hydrochloride

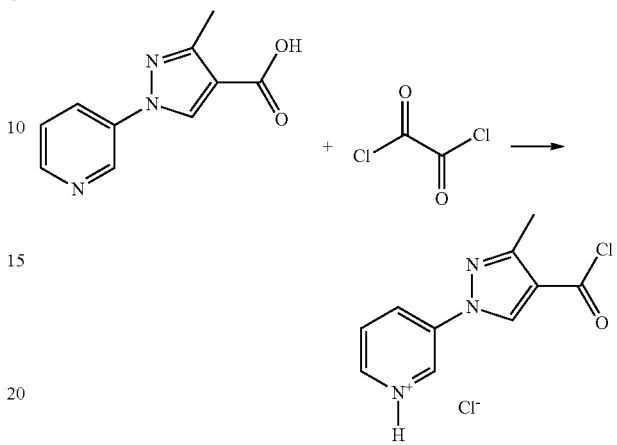

0.250 g (1.23 mmol) of 3-methyl-1-(pyridin-3-yl)-1H-pyrazole-4-carboxylic acid were initially charged in approx. 12 ml of dichloromethane, and admixed under argon with 2 drops of dimethylformamide. 0.453 g (3.56 mmol) of oxalyl chloride were added dropwise and, after the end of the addition, the mixture was stirred at room temperature for 1 h. The solution was concentrated and the residue was admixed with approx. 10 ml of toluene and concentrated. This gave a colourless solid which was converted further immediately.

Stage 4: 3-Methyl-1-(pyridin-3-yl)-N-(2,2,2-trifluoroethyl)-1H-pyrazole-4-carboxamide

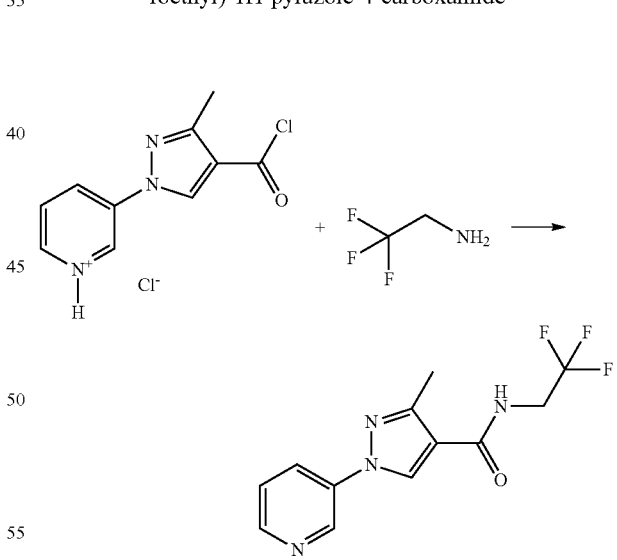

To 0.313 g (3.158 mmol) of 2,2,2-trifluoro-1-aminoethane dissolved in 20 ml of dioxane were added dropwise, under argon, 1.225 g (9.475 mmol) of N,N-diisopropylethylamine. A solution of 0.700 g (3.158 mmol) of 3-methyl-1-(pyridin-3-yl)-1H-pyrazole-4-carbonyl chloride hydrochloride in approx. 40 ml of dioxane was added (slightly exothermic). The mixture was stirred at room temperature for 12 h and then concentrated. The residue was admixed with dichloromethane/water and the aqueous phase extracted with dichloromethane. The organic phase was dried with magnesium sulphate, then concentrated and stirred with diethyl ether. The solids were filtered off.

Yield: 0.370 g (41% of theory), log P[1)] (HCOOH) 1.45

$^1$H NMR((CD$_3$)$_2$SO): 2.45 (s, 3H), 4.05 (m, 2H), 7.55 (m, 1H), 8.14 (m, 1H), 8.43 (m, 1H), 8.55(m, 1H), 8.95 (s, 1H), 9.00 (m, 1H)

Example C 1-(Pyridin-3-yl)-N-(2,2,2-trifluoroethyl)-1H-pyrazole-4-carbothioamide

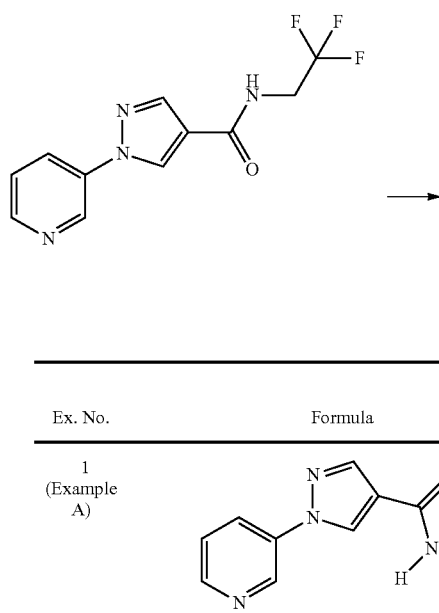

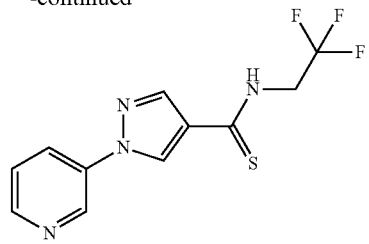

A solution of 1-(pyridin-3-yl)-N-(2,2,2-trifluoroethyl)-1H-pyrazole-4-carboxamide (100 mg, 0.37 mmol) in toluene (10 ml) was admixed with 4-methoxyphenyldithiophosphonic anhydride (82 mg, 0.20 mmol). The reaction mixture was stirred at 100° C. overnight and then cooled. A sodium hydrogen carbonate solution was added and the mixture was extracted twice with ethyl acetate. The combined organic phases were dried with magnesium sulphate and the solvent was removed under reduced pressure. The residue was purified by chromatography on silica gel (cyclohexane, ethyl acetate).

Yield: 4.800 mg (4.5% of theory), log P[1)] (HCOOH) 1.97

$^1$H NMR((CD$_3$)$_2$SO): 4.70 (m, 2H), 7.57 (m, 1H), 8.22 (m, 1H), 8.29 (s, 1H), 8.59 (m, 1H), 9.01 (s, 1H), 9.08 (m, 1H)

The table which follows lists further inventive compounds which have been prepared analogously or according to the general information in the description.

TABLE 1

| Ex. No. | Formula | M$^+$ + 1 | logP (HCOOH) | $^1$H NMR data (d$_6$-DMSO, data in ppm) |
|---|---|---|---|---|
| 1 (Example A) | | 217.1 | 0.64 | 1.13 (t, 3H), 3.28 (q, 2H), 7.56 (m, 1H), 8.03 (NH, 1H), 8.15 (s, 1H), 8.21 (m, 1H), 8.55 (m, 1H), 8.90 (s, 1H), 9.08 (m, 1H) |
| 2 (Example B) | | 285 | 1.45 | 2.45 (s, 3H), 4.05 (m, 2H), 7.55 (m, 1H), 8.14 (m, 1H), 8.43 (m, 1H), 8.55 (m, 1H), 8.95 (s, 1H), 9.00 (m, 1H) |
| 3 | | 271.1 | 1.18 | 4.07 (m, 2H), 7.56 (m, 1H), 8.24 (m, 2H), 8.57 (m, 1H), 8.70 (bt, 1H), 9.01 (s, 1H), 9.09 (m, 1H) |
| 4 | | 217.1 | 0.6 | 2.49 (s, 6H), 7.55 (m, 1H), 8.03 (s, 1H), 8.25 (m, 1H), 8.55 (m, 1H), 8.83 (s, 1H), 9.12 (m, 1H) |

TABLE 1-continued

| Ex. No. | Formula | M⁺ + 1 | logP (HCOOH) | ¹H NMR data (d$_6$-DMSO, data in ppm) |
|---|---|---|---|---|
| 5 | | 281.1 | 0.51 | 4.65 (d, 2H), 7.40-7.42 (t, 1H), 7.57-7.60 (m, 1H), 8.32-8.34 (m, 2H), 8.58 (m, 1H), 8.78 (m, 1H), 8.83-8.88 (m, 1H), 9.06 (s, 1H), 9.13 (m, 1H) |
| 6 | | 253.1 | 0.87 | 3.66 (m, 2H), 6.09 (tt, 1H), 7.57 (m, 1H), 8.22 (s, 1H), 8.24 (m, 1H), 8.46 (NH, 1H), 8.58 (m, 1H), 8.99 (s, 1H), 9.09 (m, 1H) |
| 7 | | 295.1 | 0.78 | 2.46 (s, 3H), 4.65 (m, 2H), 7.38 (t, 1H), 7.55 (m, 1H), 8.15 (m, 1H), 8.29 (m, 1H), 8.53 (m, 1H), 8.76 (m, 2H), 8.97 (s, 1H), 9.01 (m, 1H) |
| 8 | | 285.1 | 1.43 | 3.31 (s, 3H), 4.35 (q, 2H), 7.56 (m, 1H), 8.11 (m, 1H), 8.28 (m, 1H), 8.58 (m, 1H), 8.94 (s, 1H), 9.14 (m, 1H) |
| 9 | | 235.1 | 0.56 | 3.57 (dq, 2H), 4.52 (dt, 2H), 7.56 (m, 1H), 8.19 (s, 1H), 8.22 (m, 1H), 8.30 (NH, 1H), 8.57 (m, 1H), 8.95 (s, 1H), 9.08 (m, 1H) |
| 10 | | 231.1 | 0.7 | 2.31 (s, 3H), 3.04 (s, 6H), 7.53 (m, 1H), 8.20 (m, 1H), 8.51 (m, 1H), 8.65 (s, 1H), 9.08 (m, 1H) |
| 11 | | 233.1 | 0.97 | 3.27 (s, 3H), 3.77 (s, 3H), 7.57 (m, 1H), 8.14 (s, 1H), 8.29 (m, 1H), 8.57 (m, 1H), 8.90 (s, 1H), 9.15 (m, 1H) |

TABLE 1-continued

| Ex. No. | Formula | M⁺ + 1 | logP (HCOOH) | ¹H NMR data (d₆-DMSO, data in ppm) |
|---|---|---|---|---|
| 12 (Example C) | | 287.1 | 1.97 | 4.70 (m, 2H), 7.57 (m, 1H), 8.22 (m, 1H), 8.29 (s, 1H), 8.59 (m, 1H), 9.01 (s, 1H), 9.08 (m, 1H) |
| 13 | | 297 | 1.4 | 1.15 (m, 2H), 1.34 (m, 2H), 7.59 (m, 1H), 8.23-8.26 (m, 2H), 8.58 (m, 1H), 8.95 (s, 1H), 9.04 (s, 1H), 9.12 (m, 1H) |
| 14 | | 257.2 | 1.38 | 0.21 (m, 1H), 0.30 (m, 1H), 0.40 (m, 1H), 0.47 (m, 1H), 2.54 (s, 3H), 3.49 (m, 1H), 7.58 (m, 1H), 8.08 (m, 1H), 8.26 (m, 2H), 8.57 (m, 1H), 8.99 (s, 1H), 9.10 (m, 1H) |
| 15 | | 267.1 | 1.11 | 1.63 (t, 3H), 3.73 (m, 2H), 7.59 (m, 1H), 8.24-8.27 (m, 1H), 8.29 (s, 1H), 8.59 (m, 2H), 9.08 (s, 1H), 9.12 (m, 1H) |
| 16 | | 280.1 | 0.31 | 4.56 (m, 2H), 7.24-7.27 (m, 1H), 7.35 (m, 1H), 7.53-7.57 (m, 1H), 7.72-7.77 (m, 1H), 8.20-8.24 (m, 2H), 8.50 (m, 1H), 8.57 (m, 1H), 8.66 (m, 1H), 8.98 (s, 1H), 9.09 (m, 1H) |

TABLE 1-continued

| Ex. No. | Formula | M⁺ + 1 | logP (HCOOH) | ¹H NMR data (d₆-DMSO, data in ppm) |
|---|---|---|---|---|
| 17 | | 321.1 | 1.68 | 3.00 (m, 1H), 3.28 (m, 1H), 3.54 (m, 2H), 4.93 (m, 1H), 6.76 (m, 1H), 6.81 (m, 1H), 7.08 (m, 1H), 7.18 (m, 1H), 7.55 (m, 1H), 8.23 (m, 2H), 8.34 (NH, 1H), 8.56 (m, 1H), 8.95 (s, 1H), 9.08 (m, 1H) |
| 18 | | 229.1 | 0.78 | 0.55 (m, 2H), 0.68 (m, 2H), 2.81 (m, 1H), 7.57 (m, 1H), 8.18 (s, 1H), 8.24 (m, 2H), 8.56 (m, 1H), 8.97 (s, 1H), 9.10 (m, 1H) |
| 19 | | 243.1 | 1.09 | 0.62 (m, 2H), 0.85 (m, 2H), 2.99 (s, 3H), 3.16 (m, 1H), 7.58 (m, 1H), 8.16 (s, 1H), 8.30 (m, 1H), 8.57 (m, 1H), 8.99 (s, 1H), 9.17 (m, 1H) |
| 20 | | 311.1 | 1.21 | 0.88 (m, 2H), 1.04 (m, 2H), 2.09 (m, 1H), 4.66 (d, 2H), 7.56 (m, 1H), 8.23 (m, 2H), 8.58 (m, 1H), 8.89 (NH, 1H), 8.98 (s, 1H), 9.09 (m, 1H) |

TABLE 1-continued

| Ex. No. | Formula | M⁺ + 1 | logP (HCOOH) | ¹H NMR data (d₆-DMSO, data in ppm) |
| --- | --- | --- | --- | --- |
| 21 | | 285 | 1.31 | 2.53 (m, 2H), 3.49 (m, 2H), 7.59 (m, 1H), 8.20 (s, 1H), 8.25 (m, 1H), 8.49 (m, 1H), 8.99 (s, 1H), 9.11 (m, 1H) |
| 22 | | 275.1 | 0.66 | 3.40 (m, 2H), 3.82 (m, 2H), 3.94 (m, 2H), 4.95 (t, 1H), 7.59 (m, 1H), 8.24-8.27 (m, 2H), 8.39 (m, 1H), 8.58 (m, 1H), 9.04 (s, 1H), 9.11 (m, 1H) |
| 23 | | 289.2 | 0.7 | 3.23-3.32 (m, 2H), 3.40-3.84 (m, 7H), 7.55 (m, 1H), 8.12 (NH, 1H), 8.18 (s, 1H), 8.21 (m, 1H), 8.57 (m, 1H), 8.94 (s, 1H), 9.07 (m, 1H) |
| 24 | | 277.1 | 0.83 | 3.28-3.37 (m, 8H), 4.48 (m, 1H), 7.58 (m, 1H), 8.23 (s, 1H), 8.24-8.27 (m, 1H), 8.32 (m, 1H), 9.02 (s, 1H), 9.11 (m, 1H) |

TABLE 1-continued

| Ex. No. | Formula | M⁺ + 1 | logP (HCOOH) | ¹H NMR data (d₆-DMSO, data in ppm) |
|---|---|---|---|---|
| 25 | | 243.1 | 1.16 | 0.23 (m, 2H), 0.44 (m, 2H), 1.01 (m, 1H), 3.13 (t, 2H), 7.59 (m, 1H), 8.22-8.32 (m, 3H), 8.57 (m, 1H), 9.00 (s, 1H), 9.11 (m, 1H) |
| 26 | | 271.1 | 1.58/1.45 (isomers) | 0.22 (m, 1H), 030-0.50 (m, 2H), 0.98 (m, 1H), 1.22 (d, 3H), 2.43 (s, 3H), 3.50 (m, 1H), 7.52 (m, 1H), 7.61 (NH, 1H), 8.11 (m, 1H), 8.51 (m, 1H), 8.88 (s, 1H), 9.02 (m, 1H) |
| 27 | | 281.1 | 1.35 | 1.63 (t, 3H), 2.45 (s, 3H), 3.70 (m, 2H), 7.57 (m, 1H), 8.14 (m, 1H), 8.32 (m, 1H), 8.55 (m, 1H), 9.01 (m, 2H) |
| 28 | | 294.1 | 0.52 | 2.46 (s, 3H), 4.55 (d, 2H), 7.27 (m, 1H), 7.38 (m, 1H), 7.57 (m, 1H), 7.78 (m, 1H), 8.14 (m, 1H), 8.51-8.58 (m, 3H), 9.01 (m, 2H) |
| 29 | | 257.2 | 1.17 | 0.57 (m, 2H), 0.74 (m, 2H), 2.34 (s, 3H), 2.97 (s, 3H), 3.04 (m, 1H), 7.52 (m, 1H), 8.18 (m, 1H), 8.51(m, 1H), 8.75 (s, 1H), 9.07 (m, 1H) |
| 30 | | | | |

TABLE 1-continued

| Ex. No. | Formula | M+ + 1 | logP (HCOOH) | 1H NMR data (d6-DMSO, data in ppm) |
|---|---|---|---|---|
| 31 | | 335 | 1.95 | 2.45 (s, 3H), 4.13 (m, 2H), 7.58 (m, 1H), 8.14 (m, 1H), 8.57 (m, 2H), 9.01 (m, 2H) |
| 32 | | 299.1 | 1.52 | 2.44 (s, 3H), 2.52 (m, 2H), 3.47 (m, 2H), 7.57 (m, 1H), 8.13 (m, 1H), 8.15 (m, 1H), 8.54 (m, 1H), 8.88 (s, 1H), 9.01 (m, 1H) |
| 33 | | 289.1 | 0.88 | 2.44 (s, 3H), 3.39 (m, 1H), 3.83 (m, 2H), 3.94 (m, 2H), 4.94 (m, 1H), 7.58 (m, 1H), 8.07 (m, 1H), 8.15 (m, 1H), 8.54 (m, 1H), 8.99 (m, 2H) |
| 34 | | 303.1 | 0.91 | 2.44 (s, 3H), 3.22-3.40 (m, 5H), 3.47 (m, 1H), 3.58 (m, 2H), 3.75 (m, 1H), 7.56 (m, 1H), 8.03 (m, 1H), 8.15 (m, 1H), 8.54 (m, 1H), 8.95 (s, 1H), 9.13 (m, 1H) |

TABLE 1-continued

| Ex. No. | Formula | M+ + 1 | logP (HCOOH) | ¹H NMR data (d₆-DMSO, data in ppm) |
|---|---|---|---|---|
| 35 | | 291.1 | 1.04 | 2.44 (s, 3H), 3.32 (s, 6H), 3.34 (m, 2H), 4.47 (t, 1H), 7.53 (m, 1H), 7.77 (NH, 1H), 8.11 (m, 1H), 8.53 (m, 1H), 8.90 (s, 1H), 8.99 (m, 1H) |
| 36 | | 257.2 | 1.32 | 0.22-0.25 (m, 2H), 0.43-0.48 (m, 2H), 1.01 (m, 1H), 2.44 (s, 3H), 2.52 (m, 2H), 7.52-7.55 (m, 1H), 7.82 (NH, 1H), 8.11-8.14 (m, 1H), 8.53 (m, 1H), 8.87 (s, 1H), 9.00 (m, 1H) |
| 37 | | 299.1 | 1.57 | 2.33 (s, 3H), 8.29 (s, 3H), 4.37 (q, 2H), 7.55 (m, 1H), 8.24 (m, 1H), 8.53 (m, 1H), 8.54 (s, 1H), 9.11 (m, 1H) |
| 38 | | 249.1 | 0.87 | 2.45 (s, 3H), 3.54 (m, 2H), 4.53 (m, 2H), 7.55 (m, 1H), 8.15 (m, 1H), 8.23 (m, 1H), 8.55 (m, 1H), 9.00 (m, 1H) |

TABLE 1-continued

| Ex. No. | Formula | M+ + 1 | logP (HCOOH) | ¹H NMR data (d₆-DMSO, data in ppm) |
|---|---|---|---|---|
| 39 | | 231.1 | 0.91 | 1.12 (t, 3H), 2.44 (s, 3H), 3.27 (m, 2H), 7.55 (m, 1H), 7.94 (m, 1H), 8.13 (m, 1H), 8.54 (m, 1H), 9.01 (m, 1H) |
| 40 | | 228.1 | 0.52 | 4.30 (d, 2H), 7.58 (m, 1H), 8.20 (s, 1H), 8.23 (m, 1H), 8.58 (m, 1H), 8.84 (NH, 1H), 8.99 (s, 1H), 9.10 (m, 1H) |
| 41 | | 270.1 | 1.4 | 1.02 (d, 3H), 1.10 (d, 3H), 2.15 (m, 1H), 4.80 (t, 1H), 7.57 (m, 1H), 8.22 (m, 1H), 8.25 (s, 1H), 8.58 (m, 1H), 8.74 (NH, 1H), 9.03 (s, 1H), 9.10 (m, 1H) |
| 42 | | 270.1 | 1.09 | 1.74 (s, 6H), 3.16 (s, 3H), 7.56 (m, 1H), 8.09 (s, 1H), 8.26 (m, 1H), 8.57 (m, 1H), 8.93 (s, 1H), 9.13 (m, 1H) |
| 43 | | 289.1 | 1.14 | 1.39 (d, 3H), 2.43 (s, 3H), 3.66 (s, 3H), 4.48 (qu, 1H), 7.55 (m, 1H), 8.12 (m, 2H), 8.53 (m, 1H), 8.95 (s, 2H), 9.00 (m, 1H) |
| 44 | | 242.1 | 0.79 | 2.45 (s, 3H), 4.28 (d, 2H), 7.55 (m, 1H), 8.13 (m, 1H), 8.54 (m, 2H), 8.88 (s, 1H), 9.00 (m, 1H) |

TABLE 1-continued

| Ex. No. | Formula | M⁺ + 1 | logP (HCOOH) | ¹H NMR data (d₆-DMSO, data in ppm) |
|---|---|---|---|---|
| 45 | | 287.1 | 0.84 | 1.16 (m, 2H), 1.45 (m, 2H), 3.61 (s, 3H), 7.56 (m, 1H), 8.18 (s, 1H), 8.22 (m, 1H), 8.57 (m, 1H), 8.68 (NH, 1H), 8.92 (s, 1H), 9.08 (m, 1H) |
| 46 | | 267.1 | 1.12 | 2.45(s, 3H), 3.60-3.70(m, 2H), 6.11(m, 1H), 7.55-7.59 (m, 1H), 8.13-8.16(m, 1H), 8.34-8.37(t, 1H), 8.55(m, 1H), 8.98(s, 1H), 9.00(m, 1H) |
| 47 | | 311.2 | 1.63 | 1.12-1.14(m, 2H), 1.30-1.35(m, 2H), 2.43(s, 3H), 7.55-7.59(m, 1H), 8.11-8.14(m, 1H), 8.54-8.56(m, 1H), 8.71 (s, 1H), 8.96(s, 1H), 8.98-8.99(m, 1H) |
| 48 | | 325.2 | 1.43 | 0.86-0.90(m, 2H), 1.03-1.08(m, 2H), 2.06-2.12(m, 1H), 2.44(s, 3H), 4.64(d, 2H), 7.53-7.57(m, 1H), 8.12-8.15(m, 1H), 8.53-8.55(m, 1H), 8.60(t, 1H), 8.90(s, 1H), 8.99-9.00(m, 1H) |
| 49 | | 232.1 | 1.2 | 2.40(s, 6H), 2.47(s, 3H), 4.55(d, 2H), 7.11(s, 1H), 7.52-7.56(m, 1H), 8.12-8.16(m, 1H), 8.19(broad, NH), 8.52-8.54(m, 1H), 8.95(s, 1H), 9.01-9.02(m, 1H) |
| 50 | | 276.2 | 0.52 | 244(s, 3H); 3.63(s, 3H); 7.53-7.59(m, 1H); 8.13-8.16(m, 1H); 8.55-8.57(m, 1H); 8.92(s, 1H); 9.01(m, 1H); 9.16(s, 1H) |

TABLE 1-continued

| Ex. No. | Formula | M⁺ + 1 | logP (HCOOH) | ¹H NMR data (d₆-DMSO, data in ppm) |
|---|---|---|---|---|
| 51 | | 341.1 | 1.37 | 3.87(s, 6H), 4.47(d, 2H), 6.07(s, 1H), 7.53-7.57(m, 1H), 8.21-8.24(m, 2H), 8.48(broad, NH), 8.55-8.57(m, 1H), 8.98-8.99(m, 1H), 9.09-9.10(m, 1H) |
| 52 | | 321.0 | 1.69 | 4.10-4.20(m, 2H), 7.56-7.60(m, 1H), 8.25-8.29(m, 1H), 8.30(s, 1H), 8.58-8.60(m, 1H), 8.84-8.87(m, 1H), 9.10(s, 1H), 9.12-9.19(m, 1H) |
| 53 | | 254.1 | 0.76 | 1.25-1.29(m, 2H), 1.53-1.56(m, 2H), 7.54-7.58(m, 1H), 8.17(s, 1H), 8.21-8.24(m, 1H), 8.57-8.58(m, 1H), 8.96-8.97(m, 2H), 9.07-9.08(m, 1H) |
| 54 | | 290.1 | 0.79 | 2.36(s, 3H), 3.12(s, 3H), 3.58(s, 3H), 7.58(m, 1H), 8.13(m, 1H), 8.56(m, 2H), 8.65(m, 1H) |
| 55 | | 275.1 | 0.91 | 1.40(s, 3H), 3.66(s, 3H), 4.51(m, 1H), 7.54-7.58(m, 1H), 8.21-8.24(m, 2H), 8.39(d, NH), 8.56-8.58(m, 1H), 8.98-8.99(m, 1H), 9.08-9.09(m, 1H) |
| 56 | | 335.1 | 1.9 | 2.42(s, 3H), 2.90-3.10(m, 1H), 3.30-3.40(m, 1H), 3.50-3.60(m, 2H), 4.88-5.00(m, 1H), 6.20-6.40(m, 2H), 7.05-7.15(m, 1H), 7.20-7.25(m, 1H), 7.52-7.58(m, 1H), 8.10-8.20(m, 1H), 8.27-8.33(m, 1H), 8.51-8.54(m, 1H), 8.91-8.94(m, 1H), 8.98-9.03(m, 1H) |

TABLE 1-continued

| Ex. No. | Formula | M⁺ + 1 | logP (HCOOH) | ¹H NMR data (d₆-DMSO, data in ppm) |
|---------|---------|--------|--------------|-------------------------------------|
| 57 | (structure) | 391.0 | 2.56 | 2.45(s, 3H), 3.63(q, 2H), 4.25(t, 2H), 7.00-7.03(m, 1H), 7.28-7.29(m, 1H), 7.42(d, 1H), 7.52-7.57(m, 1H), 7.97-8.00(m, NH), 8.10-8.13(m, 1H), 8.52-8.54(m, 1H), 8.84(s, 1H), 8.98-8.99(m, 1H) |

1) Description of Method for Determining the LogP Values (Formic Acid Method)

The logP values reported in the table were determined according to EEC-Directive 79/831 Annex V.A8 by HPLC (High Performance Liquid Chromatography) on a reversed-phase column (C 18). Temperature: 55° C.

Eluents for the determination in the acidic range (pH 3.4):

Eluent A: acetonitrile+1 ml of formic acid/litre. Eluent B: water+0.9 ml of formic acid/litre.

Gradient: from 10% eluent A/90% eluent B to 95% eluent A/5% eluent B in 4.25 min.

The calibration was effected with unbranched alkan-2-ones (with 3 to 16 carbon atoms), whose logP values are known (determination of the logP values on the basis of the retention times by linear interpolation between two successive alkanones). The lambda-max values were determined with reference to the UV spectra from 200 nm to 400 nm in the maxima of the chromatographic signals.

2) Measurement of the NMR Spectra

The NMR spectra were
a) determined with a Bruker Avance 400, equipped with a flow probe head (volume 60 μl). The solvent used was CD₃CN or d₆-DMSO, and the reference used was tetramethylsilane (0.00 ppm).
b) determined with a Bruker Avance II 600. The solvents used were CD₃CN or d₆-DMSO, and the reference used was tetramethylsilane (0.00 ppm).

The splitting of the signals was described as follows: s (singlet), d (doublet), t (triplet), q (quartet), quin (quintet), m (multiplet).

BIOLOGICAL EXAMPLES

Example 1

*Boophilus* Microplus Test (Injection)

Solvent: dimethyl sulphoxide

To produce an appropriate active ingredient formulation, 10 mg of active ingredient is mixed with 0.5 ml of solvent stated and the concentrate is diluted to the desired concentration with solvent. The active ingredient solution is injected into the abdomen (Boophilus microplus); the animals are transferred to dishes and stored in a climate-controlled room. The action is monitored by the laying of fertile eggs.

After 7 days, the efficacy in % is determined. 100% means that no ticks have laid fertile eggs.

In this test, for example, the following compound of the Preparation Examples has an efficacy of 100% at an application rate of 20 μg/animal: 9

Example 2

Myzus Test (Spray Treatment)

Solvent:
78 parts by weight of acetone
1.5 parts by weight of dimethylformamide
Emulsifier: 0.5 part by weight of alkylaryl polyglycol ether To produce an appropriate active ingredient formulation, 1 part by weight of active ingredient is mixed with the amounts of solvent and emulsifier specified and the concentrate is diluted to the desired concentration with emulsifier-containing water.

Chinese cabbage leaf slices (*Brassica pekinensis*) infested by all stages of the green peach aphid (*Myzus persicae*) are sprayed with an active ingredient formulation of the desired concentration.

After 6 days, the efficacy in % is determined. 100% means that all aphids have been killed; 0% means that no aphids have been killed.

In this test, for example, the following compound of the Preparation Examples has efficacy of 80% at an application rate of 500 g/ha: 12

In this test, for example, the following compounds of the Preparation Examples have efficacy of 90% at an application rate of 50 g/ha: 4, 30, 52, 53, 55

In this test, for example, the following compounds of the Preparation Examples have efficacy of 100% at an application rate of 500 g/ha: 1, 2, 3, 5, 6, 7, 8, 9, 10, 13, 14, 15, 16, 18, 19, 20, 21, 22, 23, 24, 25, 26, 27, 28, 29, 31, 32, 33, 34, 35, 36, 37, 38, 39, 40, 41, 42, 43, 45, 46, 47, 48, 49, 50, 54, A-4

Example 3

Phaedon Test (Spray Treatment)

Solvent:
78.0 parts by weight of acetone
1.5 parts by weight of dimethylformamide
Emulsifier: 0.5 part by weight of alkylaryl polyglycol ether To produce an appropriate active ingredient formulation, 1 part by weight of active ingredient is mixed with the amounts of solvent and emulsifier specified and the concentrate is diluted to the desired concentration with emulsifier-containing water.

Chinese cabbage leaf slices (*Brassica pekinensis*) are sprayed with an active ingredient formulation of the desired concentration and, after drying, populated with larvae of the mustard beetle (*Phaedon cochleariae*).

After 7 days, the efficacy in % is determined. 100% means that all beetle larvae were killed; 0% means that no beetle larvae were killed.

In this test, for example, the following compound of the Preparation Examples has efficacy of 100% at an application rate of 500 g/ha: 3

The invention claimed is:

1. A compound of the formula (I)

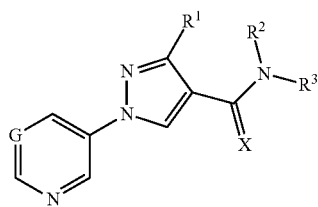

in which
G is CH, C-halogen, C-nitro, C-cyano, C—$C_1$-$C_6$-haloalkyl, C—$C_3$-$C_6$-cycloalkyl, C—$C_1$-$C_6$-alkoxy, or C—$C_1$-$C_6$-haloalkoxy, $R^1$ is hydrogen, $C_1$-$C_6$-alkyl, $C_1$-$C_6$-haloalkyl, $C_3$-$C_6$-cycloalkyl, halogen, cyano, $C_1$-$C_6$-alkoxy, $C_1$-$C_6$-haloalkoxy, amino, $C_1$-$C_6$-alkylamino, di($C_1$-$C_6$)-alkylamino or $C_1$-$C_6$-thioalkyl, X is oxygen or sulphur, $R^2$ is a radical selected from the group consisting of hydrogen, $C_1$-$C_6$-alkyl, $C_1$-$C_6$-haloalkyl, $C_1$-$C_4$-alkoxy, $C_1$-$C_4$-haloalkoxy, $C_2$-$C_4$-alkenyl, $C_1$-$C_4$-alkoxy-$C_1$-$C_4$-alkyl, optionally halogen-substituted $C_1$-$C_4$-alkylcarbonyl, optionally halogen-substituted $C_1$-$C_4$-alkoxycarbonyl and optionally halogen-substituted $C_3$-$C_6$-cycloalkylcarbonyl,
and $R^3$ is a radical selected from the group consisting of hydrogen, $C_1$-$C_6$-alkyl, $C_1$-$C_6$-haloalkyl, cyano-$C_1$-$C_6$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_6$-alkoxy, $C_1$-$C_6$-haloalkoxy, optionally halogen-substituted $C_1$-$C_6$-alkoxy-$C_1$-$C_6$-alkyl, optionally halogen-substituted bis($C_1$-$C_6$-alkoxy)-$C_1$-$C_6$-alkyl, optionally halogen-substituted $C_1$-$C_6$-alkylthio-$C_1$-$C_6$-alkyl, optionally halogen-substituted $C_1$-$C_4$-alkylcarbonyl-$C_1$-$C_6$-alkyl, optionally halogen-substituted $C_1$-$C_6$-alkylsulphinyl-$C_1$-$C_6$-alkyl, optionally halogen-substituted $C_1$-$C_6$-alkyl sulphonyl-$C_1$-$C_6$-alkyl, optionally halogen-substituted $C_1$-$C_6$-alkoxycarbonyl-$C_1$-$C_6$-alkyl, $C_1$-$C_6$-alkoxycarbonylamino optionally $C_1$-$C_6$-alkyl-substituted on the nitrogen, $C_2$-$C_4$-alkynyloxy, $C_2$-$C_4$-alkynyloxycarbonyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, or $C_1$-$C_6$-haloalkoxycarbonyl-substituted $C_3$-$C_6$-cycloalkyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, or $C_1$-$C_6$-haloalkoxycarbonyl-substituted $C_3$-$C_6$-cycloalkylcarbonyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, or $C_1$-$C_6$-haloalkoxycarbonyl-substituted $C_3$-$C_6$-cycloalkyl-$C_1$-$C_6$-alkyl, optionally halogen-, cyano-, $C_1$-$C_6$-alkyl-, $C_1$-$C_6$-alkoxy- or $C_1$-$C_6$-haloalkoxy-substituted aryl-$C_1$-$C_6$-alkyl, optionally in the aryl moiety, halogen-substituted aryloxy-$C_1$-$C_6$-alkyl, and $NR^4R^5$ in which $R^4$ and $R^5$ are each independently a radical selected from the group consisting of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxycarbonyl,
and a salt and a N-oxide of the compound of the formula (I).

2. A composition, comprising at least one compound of the formula (I) according to claim 1 and one or more extenders, surfactants, and combinations thereof.

3. A method for controlling insects or arthropods, comprising contacting an effective amount of a compound of the formula (I) according to claim 1 with one or more insects or arthropods, their habitat, or combinations thereof.

4. The compound according to claim 1,
in which
G is CH, C-halogen, C-nitro, C-cyano, C—$C_1$-$C_4$ alkyl, C—$C_1$-$C_4$-haloalkyl, C—$C_3$-$C_6$-cycloalkyl, C—$C_1$-$C_4$-alkoxy, or C—$C_1$-$C_4$-haloalkoxy, $R^1$ is hydrogen, $C_1$-$C_4$-alkyl, $C_1$-$C_4$-haloalkyl, $C_3$-$C_6$-cycloalkyl, halogen, cyano, $C_1$-$C_4$-alkoxy, $C_1$-$C_4$-haloalkoxy, amino, $C_1$-$C_4$-alkylamino, di($C_1$-$C_4$)-alkylamino or $C_1$-$C_4$-thioalkyl, X is oxygen or sulphur, $R^2$ is a radical selected from the group consisting of hydrogen, $C_1$-$C_4$-alkyl, $C_1$-$C_4$-haloalkyl, $C_1$-$C_4$-alkoxy, $C_2$-$C_3$-alkenyl, $C_1$-$C_2$-alkoxy-$C_1$-$C_2$-alkyl, $C_1$-$C_2$-alkylcarbonyl, $C_1$-$C_2$-alkoxycarbonyl, and in each case optionally halogen-substituted cyclopropylcarbonyl, cyclopentylcarbonyl or cyclohexylcarbonyl, $R^3$ is a radical selected from the group consisting of hydrogen, $C_1$-$C_4$-alkyl, $C_1$-$C_5$-haloalkyl, cyano-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, optionally halogen-substituted $C_1$-$C_2$-alkoxy-$C_1$-$C_4$-alkyl, optionally halogen-substituted bis($C_1$-$C_2$-alkoxy)-$C_1$-$C_4$-alkyl, optionally halogen-substituted $C_1$-$C_4$-alkylthio-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, optionally halogen-substituted $C_1$-$C_4$-alkoxycarbonyl-$C_1$-$C_4$-alkyl, $C_1$-$C_4$-alkoxycarbonylamino optionally $C_1$-$C_4$-alkyl-substituted on the nitrogen, $C_2$-$C_4$-alkynyloxy, $C_2$-$C_4$-alkynyloxycarbonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, or $C_1$-$C_4$-haloalkoxycarbonyl-substituted $C_3$-$C_6$-cycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, or $C_1$-$C_4$-haloalkoxycarbonyl-substituted $C_3$-$C_6$-cycloalkylcarbonyl, optionally halogen-, cyano-, $C_1$-$C_4$-haloalkyl-, $C_1$-$C_4$-alkoxy-, $C_1$-$C_4$-haloalkoxy-, $C_1$-$C_4$-alkoxycarbonyl-, or $C_1$-$C_4$-haloalkoxycarbonyl-substituted $C_3$-$C_6$-cycloalkyl-$C_4$-$C_4$-alkyl, optionally halogen-, cyano-, $C_1$-$C_4$-alkyl-, $C_1$-$C_4$-haloalkyl-, $C_1$-$C_4$-alkoxy- or $C_1$-$C_4$-haloalkoxy-substituted aryl-$C_1$-$C_4$-alkyl, aryloxy-$C_1$-$C_4$-alkyl optionally halogen-substituted in the aryl moiety.

5. The compound according to claim 1,
in which

G is CH, C-halogen, C-cyano, C—$CH_3$, C—$CF_3$, C-cyclopropyl, C—$OCH_3$, or C—$OCF_3$, $R^1$ is hydrogen, methyl, trifluoromethyl, cyclopropyl, halogen, cyano, methoxy, trifluoromethoxy, amino, methylamino, or dimethylamino, X is oxygen or sulphur, $R^2$ is a radical selected from the group consisting of hydrogen, methyl, ethyl, $CH_2CF_3$, $CH_2CF_2CH_3$, $CH_2CHF_2$, $CH_2CF_2CHF_2$, $CH_2CH_2F$, $CH_2$—$CHFCH_3$, $CH_2CF_2Br$, $CH_2CFCl_2$, $CH(CH_3)CH_2F$, $CH_2CCl_3$, $CH_2CClF_2$, $CH_2CH_2CH_2F$, $CH_2CH(CH_3)Cl$, $CHCF_3CH(CH_3)_2$, $CH(CF_3)_2$, $CH_2CH_2Cl$, $CHCF_3CH_2CH_2CH_3$, $CH_2CF_2CF_3$, methoxy, ethoxy, vinyl, $CH_2OCH_3$, $CH_2OCH_2CH_3$, methylcarbonyl, ethylcarbonyl, methoxycarbonyl, ethoxycarbonyl, cyclopropylcarbonyl and fluorocyclopropylcarbonyl,
and $R^3$ is a radical selected from the group consisting of hydrogen, methyl, ethyl, $CH_2CF_3$, $CH_2CH_2CF_3$, $CH_2CF_2CH_3$, $CH_2CHF_2$, $CH_2CF_2CHF_2$, $CH_2CH_2F$, $CH_2CHFCH_3$, $CH_2CF_2Br$, $CH_2CFCl_2$, $CH(CH_3)CH_2F$, $CH_2CCl_3$, $CH_2CClF_2$, $CH_2CH_2CH_2F$, $CH_2CH(CH_3)Cl$, $CHCF_3CH(CH_3)_2$, $CH(CF_3)_2$, $CH_2CH_2Cl$, $CHCF_3CH_2CH_2CH_3$, $CH_2CF_2CF_3$, $C(CH_3)_2CN$, $CH(CN)CH(CH_3)_2$, $CH_2CN$, $CH_2CH_2CN$, vinyl, $C(CH_3)_2CCH$, $CH_2CCCH_3$, methoxy, ethoxy, $CH_2CH(OCH_3)_2$, $CH_2CH(CH_3)(OCH_3)$, $CH_2C(CH_3)_2(OCH_3)$, $CH(CH_3)CH(OCH_3)_2$, $CH_2C(CH_3)(OCH_3)_2$, $C(CH_3)_2$—$CH_2SCH_3$, $CH_2CH_2SCH_3$, $CHCH_3CH_2SCH_3$, optionally halogen-substituted $C_1$-$C_4$-alkyl-carbonyl-$C_1$-$C_4$-alkyl, $CH_3SO_2CH_2C(CH_3)_2$, $CH_3SO_2CH_2CHCH_3$, propargyloxy, cyclopropyl, cyanocyclopropyl, fluorocyclopropyl, trifluoromethylcyclopropyl, trifluoromethylcyclohexyl, methoxycarbonylcyclopropyl, fluorocyclopropylcarbonyl, cyclopropylmethyl, 1-cyclopropylethyl, cyclohexylmethyl, 1-cyano-1-cyclopropyleth-1-yl, optionally halogen-, cyano-, methyl-, ethyl-, methoxy- or ethoxy-substituted benzyl, methoxycarbonylethyl, methoxycarbonylamino, 4,6-dimethoxypyrimid-2-ylmethyl, 2-(2,5-dichlorophenoxy)ethyl and N-methyl-N-methoxycarbonyl-amino.

* * * * *